(12) United States Patent
Elor et al.

(10) Patent No.: US 12,260,010 B2
(45) Date of Patent: Mar. 25, 2025

(54) SYSTEM AND METHOD FOR UTILIZING IMMERSIVE VIRTUAL REALITY IN PHYSICAL THERAPY

(71) Applicants: Aviv Elor, Walnut Creek, CA (US); Michael Ora Powell, Campbell, CA (US); Ash Seymour Robbins, Santa Cruz, CA (US)

(72) Inventors: Aviv Elor, Walnut Creek, CA (US); Michael Ora Powell, Campbell, CA (US); Ash Seymour Robbins, Santa Cruz, CA (US)

( * ) Notice: Subject to any disclaimer, the term of this patent is extended or adjusted under 35 U.S.C. 154(b) by 0 days.

(21) Appl. No.: 17/868,743

(22) Filed: Jul. 19, 2022

(65) Prior Publication Data

US 2024/0028106 A1    Jan. 25, 2024

(51) Int. Cl.
G06F 3/01 (2006.01)
G06T 13/40 (2011.01)
G06T 19/00 (2011.01)
G16H 20/30 (2018.01)

(52) U.S. Cl.
CPC .............. G06F 3/011 (2013.01); G06T 13/40 (2013.01); G06T 19/006 (2013.01); G16H 20/30 (2018.01)

(58) Field of Classification Search
None
See application file for complete search history.

(56) References Cited

U.S. PATENT DOCUMENTS

| | | | |
|---|---|---|---|
| 2014/0067768 A1* | 3/2014 | Fateh | G06F 16/2228 707/684 |
| 2020/0038709 A1* | 2/2020 | Vissa | A63B 71/0619 |
| 2020/0279112 A1* | 9/2020 | Wells | G02B 27/0176 |

* cited by examiner

*Primary Examiner* — Yi Wang
(74) *Attorney, Agent, or Firm* — Patrick Reilly

(57) ABSTRACT

A system and method for utilizing virtual reality technology to provide and improve physical therapy care. Virtual reality devices may be utilized to facilitate telehealth visits in a three-dimensional medium where a digital avatar moves in accordance with the movement of a patient wearing a virtual reality device. Virtual reality devices may be used to provide and monitor exercises prescribed for a physical therapy patient. Virtual reality devices may be used to record, model, and analyze motion patterns of a physical therapy patient to assess relevant physical capability such as balance or motor control.

24 Claims, 14 Drawing Sheets

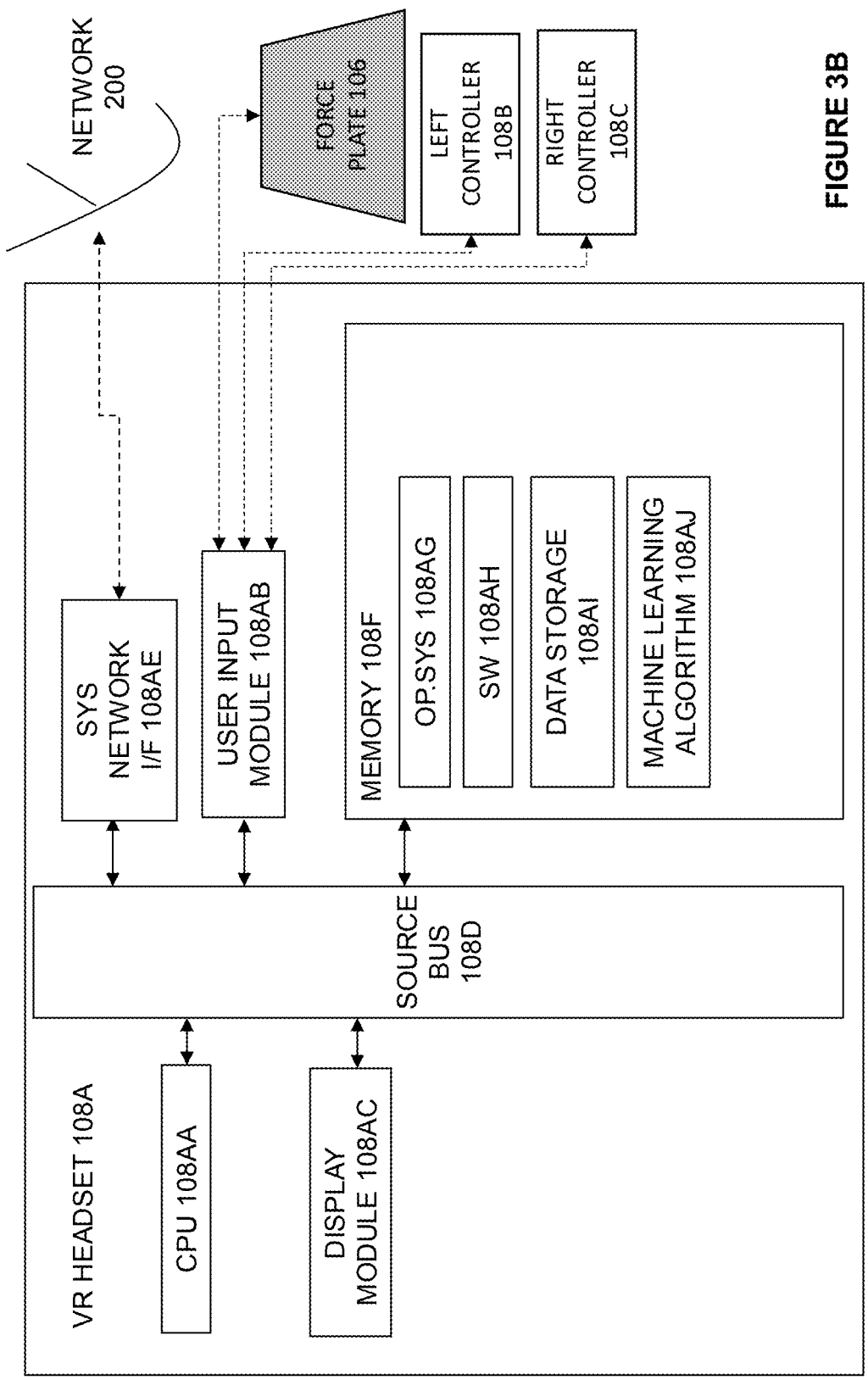

SYSTEM AND METHOD FOR UTILIZING IMMERSIVE VIRTUAL REALITY IN PHYSICAL THERAPY

STATEMENT REGARDING FEDERALLY SPONSORED RESEARCH OR DEVELOPMENT

The present invention was made with U.S. Government support under Grant (Phase I SBIR) No. 2111847 awarded by the U.S. National Science Foundation for the operation of Immergo Labs, Inc. The U.S. Government has no rights to the present invention.

BACKGROUND OF THE INVENTION

Field of the Invention

The field of the invention relates generally to therapeutic application of virtual reality technology, and specifically to use of virtual reality equipment for assessment of balance capability in physical therapy patients.

Background Art

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Physical therapy, or physiotherapy, is the medical discipline addressing illnesses, injuries, or disabilities that limit a person's ability to move and perform functional activities in their daily life. Some reasons a patient might receive physical therapy could include recovering range of motion lost to an injury or as recovery from surgery, developing facility with a newly received prosthetic, or coping with a medical condition that affects one's proprioception or motor control such as a brain injury, stroke, Alzheimer's disease, multiple sclerosis, Parkinson's disease, or many others. A key concern in this field is assessing the patient's current motor capabilities, such as strength, flexibility, ability to balance, and motor control.

The field of video gaming is entertaining and interactive, and has also been shown to provide therapeutic benefits, such as honing motor skills and providing engaging challenges for players to overcome. More recent technology includes sensors and gyroscopes enabling a device to detect and codify a player's physical motion, creating such video gaming experiences as swinging a game controller like a baseball bat and having a virtual baseball on a screen 'get hit' and go flying as a result of the motion, or dancing with a controller and having a digitally-generated avatar perform the same dance moves. Bringing video games to practice of therapy is beginning to show promise in many areas, as the medium is versatile and multifaceted.

Accordingly, there is a long-felt need to improve assessment and providing of physical therapy at least pertaining to balance, and to apply the innovative capabilities of virtual reality consoles to this endeavor.

BRIEF SUMMARY OF THE INVENTION

Towards these and other objects of the method of the present invention (hereinafter, "the invented method") that are made obvious to one of ordinary skill in the art in light of the present disclosure, what is provided is a system and method for providing physical therapy utilizing virtual reality technology.

In a first preferred operational practice, a clinic or similar may set up a station including at least a pressure plate, a virtual reality device such as a unit comprising a headset and controllers, which may also include further elements such as a pressure plate or a desktop computer connected to both the virtual reality device and the pressure plate if present. A physical therapy patient may stand on the pressure plate, wear the virtual reality headset and hold the controllers, and follow directions provided by a therapist or even by an interface or program presented by the VR headset screen. The patient may be set tasks or challenges within the virtual environment presented by the headset, requiring movements and actions that demonstrate various levels or varieties of motor capability, all within the context of a user-friendly game played in a safe environment.

In a second preferred operational practice, a therapist practitioner utilizing a first virtual reality device might meet virtually with a patient utilizing a second virtual reality device, like a telehealth visit in 3D. Since so much of physical therapy pertains to observing and coaching motion of the patient's body, a virtual environment wherein the therapist's and patient's motions are mirrored by virtual avatars may provide a more conducive medium than a two-dimensional medium such as a telehealth call over a service such as WebEx or Zoom. The therapist and patient use the technology to observe and analyze the motion of the patient's body through data generated by motion of the patient's virtual reality equipment, and the therapist may prescribe exercises which can be done while supervised by the therapist, or 'taken home' to do independently, by the patient using the virtual reality equipment interface, including the possibility of providing or downloading premade physical therapy software or games, and structuring the patient's 'take home' exercises with these additional tools.

In a preferred method for assessing a patient's balance proficiency utilizing the invention, the patient may be asked to attempt to stand perfectly still for a set length of time, such that the sensors of the virtual reality equipment (and a pressure plate, if available) can measure the extent to which the patient might 'sway' or 'wobble' a little even while standing still, and the computer can collect this data, model and analyze the detected sway pattern, and even compare this patient's sway pattern against one or more baselines or profiles.

This invention may provide at least the benefit of a new physiotherapy tool that therapists can utilize as they deem necessary, as one more available option for assessment, ongoing analysis, or treatment. It is noted also that this may provide computer-enabled exercises and structure that can help patients progress more easily and receive better care, while also potentially saving time for a live physical therapist at least by providing analytic support and improving communication. Additionally, it's noted that certain patients may find it easier or more comfortable to engage with and relax in a virtual environment and explore their physical capabilities in that context. It's further noted that such a system may be beneficial in telehealth applications, and also that such a system, particularly with physical therapy programs designed by licensed physiotherapists preinstalled or non-local therapists available for virtual appointments, could be very useful as a vehicle for supplying improved physical therapy capability to a remote location, such as for augmenting the capabilities of a general-purpose medical clinic in a rural area where actual physical therapy practitioners may be few and far between, or care otherwise limited or difficult to access.

Certain preferred embodiments of the invention may include a client device comprising at least: an augmented reality patient set ("patient set"), the patient set comprising a head set and an additional positional feedback device, wherein the patient set is configured to be worn by a human patient and to generate and transmit positional information related to a dynamic positioning of the human patient's body; one or more processors bi-directionally communicatively coupled by a communications module with the patient set; a memory bi-directionally communicatively coupled by the communications module with the one or more processors and the patient set, the memory storing software executable instructions executing on the client device, the software executable instructions when executed by the one or more processors cause the client device to: access a video segment directing the client system to dynamic visual rendering of a patient avatar derived from and dynamically responsive to positional information received from the patient set; transmit to the headset a sequence of data frames from a data stream program, wherein each data frame including positioning information of a modeling avatar for rendering by the headset, the modelling avatar adapted to dynamically present to the patient via the headset aspects of a personalized therapeutic movement path; and display an interactive dynamic overlay of the modelling avatar over the patient avatar by the headset, the interactive overlay displayed in association with dynamically updated positional information, wherein the dynamically updated position information of the patient set is derived from the positional data generated by the patient set and received by the one or more processors.

This client device might also include the data stream program containing information derived from dynamically generated positional data received previous to a therapeutic session. The client device might also include the data stream program containing information that modifies a dynamic instanton of the modelling avatar on the basis of dynamically generated positional data received from the patient set during a same therapeutic session. The client device might also include the data stream program containing information that modifies a dynamic instanton of the modelling avatar on the basis of dynamically generated positional data received from the patient set during an earlier observed therapeutic session.

The patient set may be dynamically generated the positional data received previous to the therapeutic session. The data stream program may contain information describing a full range of preferred motion personalized for an identified patient. The data stream program may contain information describing a modified range of a preferred limited range of motion personalized for an identified patient. The data stream program may contain information enabling the client device to dynamically vary a rendered range of motion on the bases of positional data received within a same therapeutic session. The client device may further comprise the one or more processors receiving an informational update to the data stream program, wherein the informational update provides information the client device that enables a revision of the positioning information of a modeling avatar adapted for rendering by the headset. The update information may be received and applied by the client device during a same therapeutic session. The memory may contain additional software executable instructions that when executed by the one or more processors enable the client device to provide alternate avatar positioning information of two or more modeling avatars for rendering by the headset, wherein each modelling avatar is adapted to dynamically present to the patient via the headset aspects of an alternate personalized therapeutic movement path.

At least a portion of the software executable instructions may be received and applied during a same therapeutic session. The client device may be adapted to and at least partially renders a virtual reality environment by means of the patient set.

The device may further comprise: the patient set further comprising an audio data rendering module ("audio module") coupled with the one or more processors; additional instructions of the software executable instructions that when executed by the one or more processors cause the client device to transmit audio data to the audio module. The audio data may be generated from the data stream program. The audio data may be sourced externally from the client device. Each data stream program of the client device may include a respective video sequence information and a respective audio sequence information, and the audio sequence information is adapted for rendering by the patient set audio module. The client device may include the interactive dynamic overlay of the modelling avatar including a Hypertext Markup Language (HTML) overlay.

An invented method of rendering interactive overlays within a therapeutic session may comprise the following: accessing by one or more processors a video segment directing a client system to dynamic visual render a patient avatar at a headset information partially derived from and dynamically responsive to positional information received from the headset; transmitting to the headset a sequence of data frames from a data stream program, wherein each data frame including positioning information of a modeling avatar for rendering by the headset, the modelling avatar adapted to dynamically present to the patient via the headset aspects of a personalized therapeutic movement path; displaying an interactive dynamic overlay of the modelling avatar over the patient avatar by the headset, the interactive overlay displayed in association with dynamically updated positional information, wherein the dynamically updated position information of the patient set is derived from the positional data generated by the patient set and received by the one or more processors. This method might further comprise establishing, by the one or more processors, a communication channel with a session management system, and wherein at least a portion of the sequence of data frames rendered by the headset are received by client device over the established communication channel. The method might further include the one or more processors being adapted to at least partially render a virtual reality environment by means of the headset.

Further additional or alternative aspects of the invention might include a non-transitory computer-readable medium comprising computer code instructions stored thereon, the computer code instructions, when executed by one or more processors, cause the one or more processors to: access a video segment directing a client system to dynamic visual render a patient avatar at a headset information partially derived from and dynamically responsive to positional information received from the headset; transmit to the headset a sequence of data frames from a data stream program, wherein each data frame including positioning information of a modeling avatar for rendering by the headset, the modelling avatar adapted to dynamically present to the patient via the headset aspects of a personalized therapeutic movement path; display an interactive dynamic overlay of the modelling avatar over the patient avatar by the headset, the interactive overlay displayed in association with dynamically updated positional information, wherein the dynamically updated position information of the patient set is derived from the positional data generated by the patient set and received by the one or more processors.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE SEVERAL VIEWS OF THE DRAWING(S)

The detailed description of some embodiments of the invention is made below with reference to the accompanying figures, wherein like numerals represent corresponding parts of the figures.

FIG. 3B is a hardware diagram presenting the virtual reality device of FIG. 1;

DETAILED DESCRIPTION OF THE INVENTION

Figure 1:
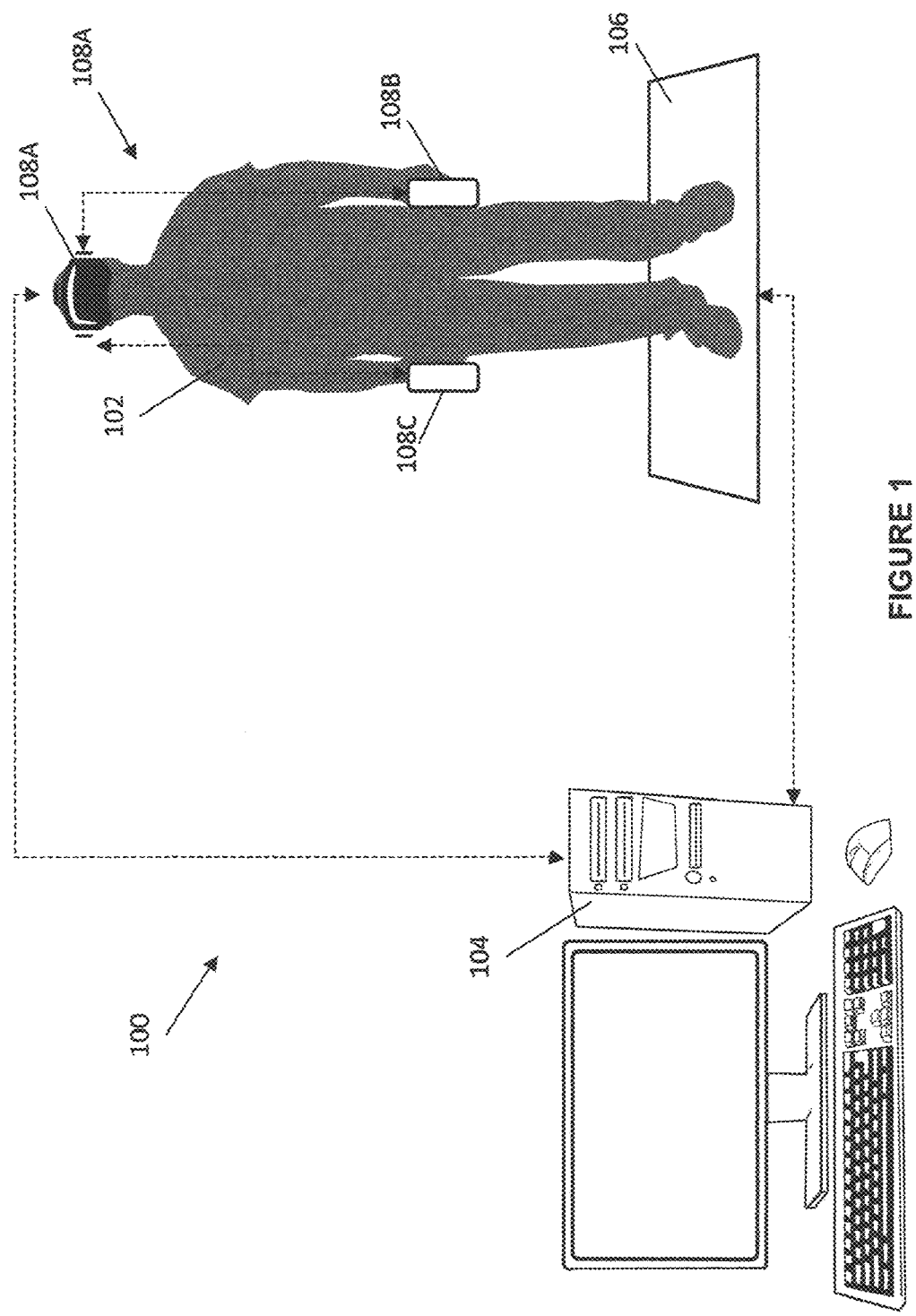
FIG. 1 is a diagram presenting a first embodiment of an invented system for utilizing VR technology in physical therapy, comprising at least a virtual reality device, and optionally further including a computing device and/or an optional force plate.

In the following detailed description of the invention, numerous details, examples, and embodiments of the invention are described. However, it will be clear and apparent to one skilled in the art that the invention is not limited to the embodiments set forth and that the invention can be adapted for any of several applications.

It is to be understood that this invention is not limited to particular aspects of the present invention described, as such may, of course, vary. It is also to be understood that the terminology used herein is for the purpose of describing particular aspects only, and is not intended to be limiting, since the scope of the present invention will be limited only by the appended claims. Methods recited herein may be carried out in any order of the recited events which is logically possible, as well as the recited order of events.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the range's limits, an excluding of either or both of those included limits is also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

When elements are referred to as being "connected" or "coupled," the elements can be directly connected or coupled together or one or more intervening elements may also be present. In contrast, when elements are referred to as being "directly connected" or "directly coupled," there are no intervening elements present.

In the specification and claims, references to "a processor" include multiple processors. In some cases, a process that may be performed by "a processor" may be actually performed by multiple processors on the same device or on different devices. For the purposes of this specification and claims, any reference to "a processor" shall include multiple processors, which may be on the same device or different devices, unless expressly specified otherwise.

The subject matter may be embodied as devices, systems, methods, and/or computer program products. Accordingly, some or all of the subject matter may be embodied in hardware and/or in software (including firmware, resident software, micro-code, state machines, gate arrays, etc.) Furthermore, the subject matter may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an instruction execution system. Note that the computer-usable or computer-readable medium could be paper or another suitable medium upon which the program is printed, as the program can be electronically captured, via, for instance, optical scanning of the paper or other medium, then compiled, interpreted, of otherwise processed in a suitable manner, if necessary, and then stored in a computer memory.

When the subject matter is embodied in the general context of computer-executable instructions, the embodiment may comprise program modules, executed by one or more systems, computers, or other devices. Generally, program modules include routines, programs, objects, components, data structures, etc. that perform particular tasks or implement particular abstract data types. Typically, the functionality of the program modules may be combined or distributed as desired in various embodiments.

Additionally, it should be understood that any transaction or interaction described as occurring between multiple computers is not limited to multiple distinct hardware platforms, and could all be happening on the same computer. It is understood in the art that a single hardware platform may host multiple distinct and separate server functions.

Throughout this specification, like reference numbers signify the same elements throughout the description of the figures.

Referring now generally to the Figures, and particularly to FIG. 1, FIG. 1 is a diagram presenting a basic overview of hardware aspects of an invented movement assessment system 100 ("the system 100"), as operated by a patient 102. The system 100 may include at least some or all of the following hardware: a computing device 104 ("the device 104") such as but not limited to a desktop computer or laptop, a force plate 106, and a set of virtual reality gear 108 ("the VR gear 108") such as the model presented here which further comprises a VR headset 108A, a left VR controller 108B, and a right VR controller 108C ("the VR controllers 108B&C"). In preferred operation, the patient 102 puts on the VR gear 108 and stands on the optional force plate 106 if included, so that the motions of the patient 102 as directed by a therapist (not shown) or by the VR gear 108 interface can be captured by the device 104 via the optional force plate 106 and the VR gear 108 and analyzed.

It is noted that, depending upon the application and hardware capability, the VR gear 108 alone may perform some or all of the preferred aspects of the invented method and minimize or even eliminate the necessity of including external devices such as the computing device 104 or the force plate 106 in every implementation; for the sake of completeness, these items are still presented herein sometimes where they might optionally or sometimes be included. It is further noted that force plates in particular are generally expensive and difficult to obtain and set up, and that making physical therapy at least as accessible as a VR headset is, lowering barriers to accessing care that may result from distance or expense, is a notable benefit of the described invention. Accordingly, some more established implementations, such as lab settings or large physical therapy practices, might set up a more 'comprehensive' version of the system 100, such as one with the force plate 106 and additional devices or computers attached, and may generate more complete or nuanced data that way, while machine learning based on some of that high-quality data may benefit or empower AI analysis of comparatively less comprehensive data gathered by the VR gear 108 alone as utilized by a smaller practice or by an individual seeking treatment remotely.

Figure 2:
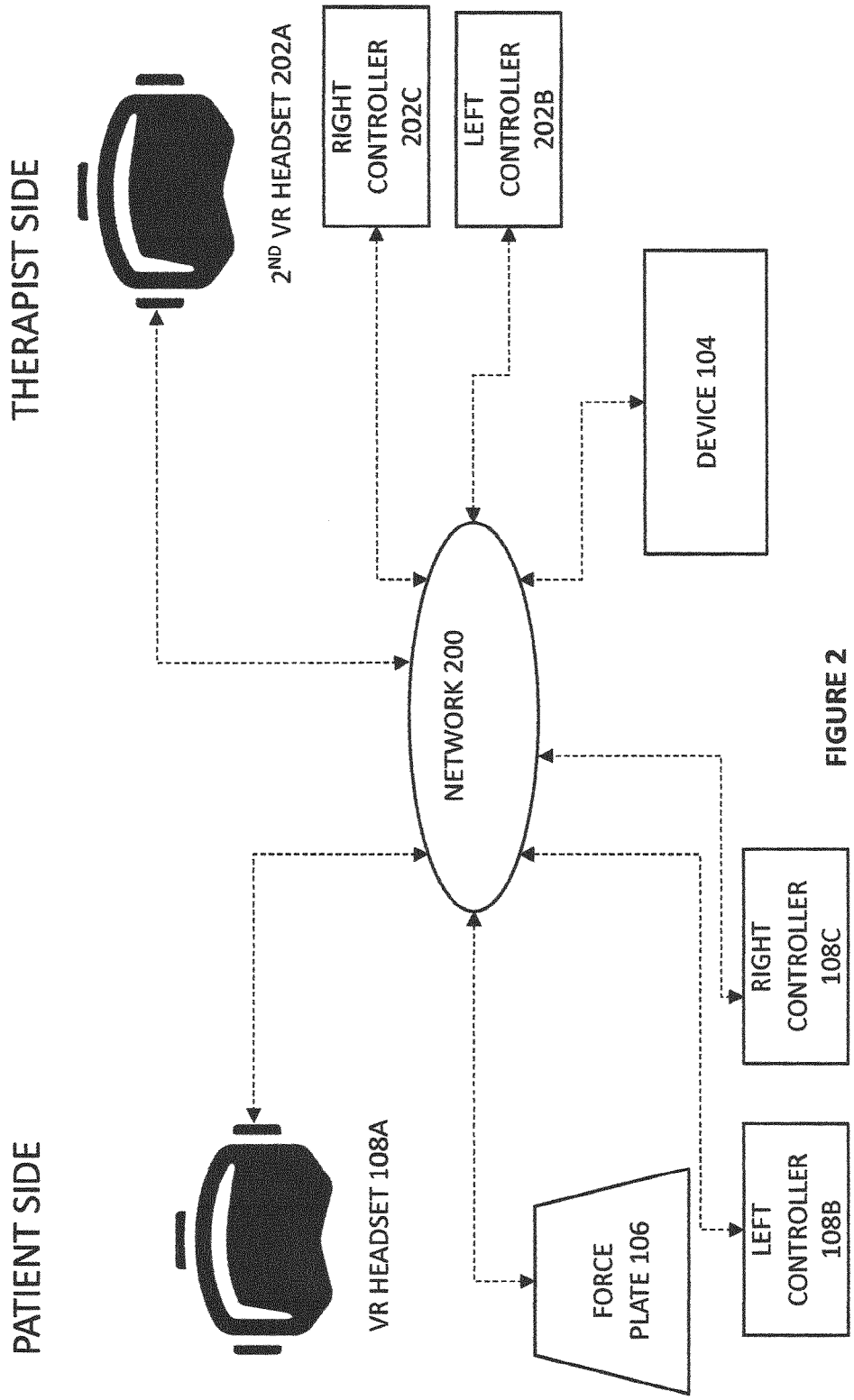
FIG. 2 is a diagram presenting an electronic communications network connecting elements of a second embodiment of an invented system for utilizing VR technology in physical therapy.
Figure 3A:
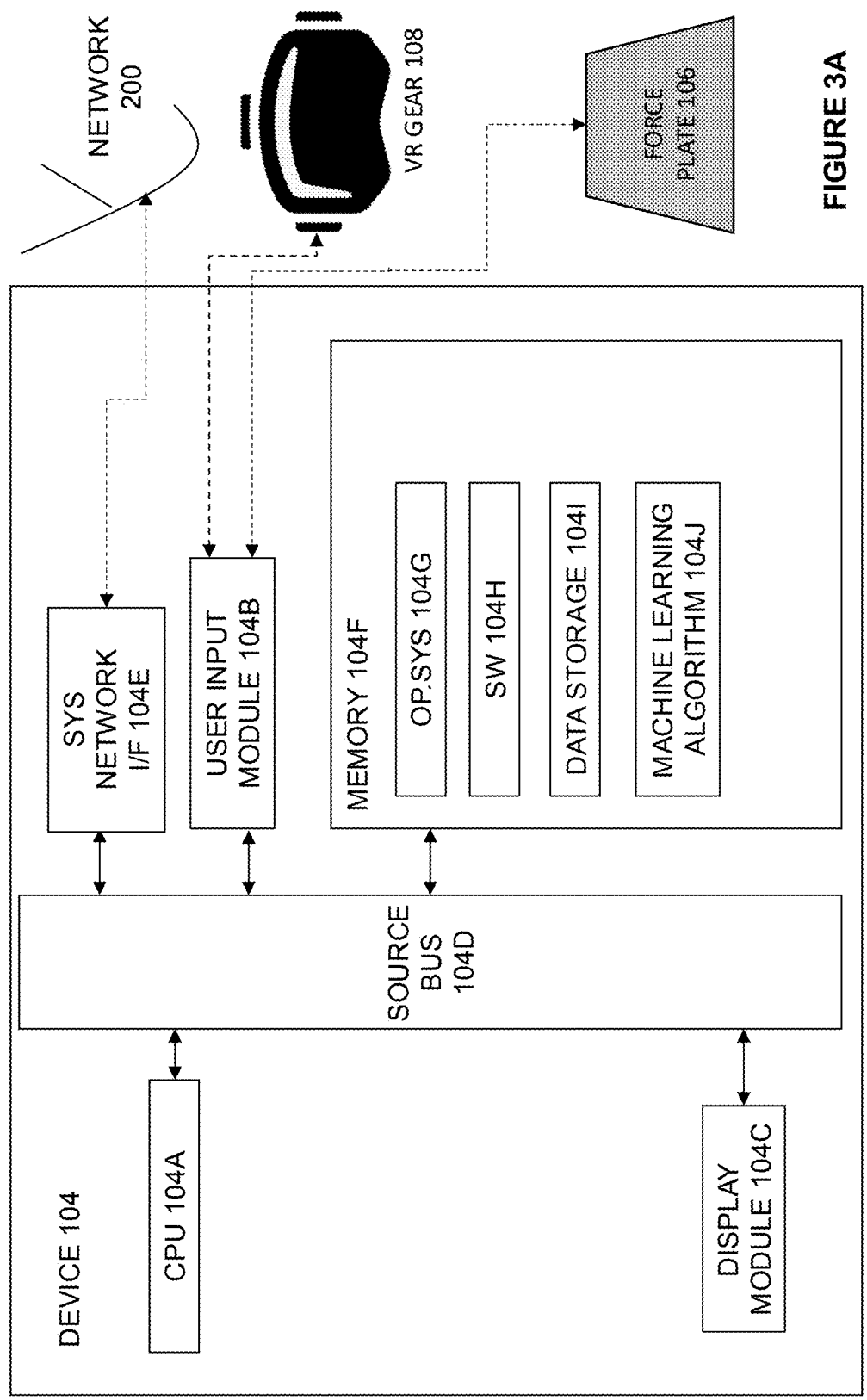
FIG. 3A is a hardware diagram presenting the computing device of FIG. 1.
Figure 3C:
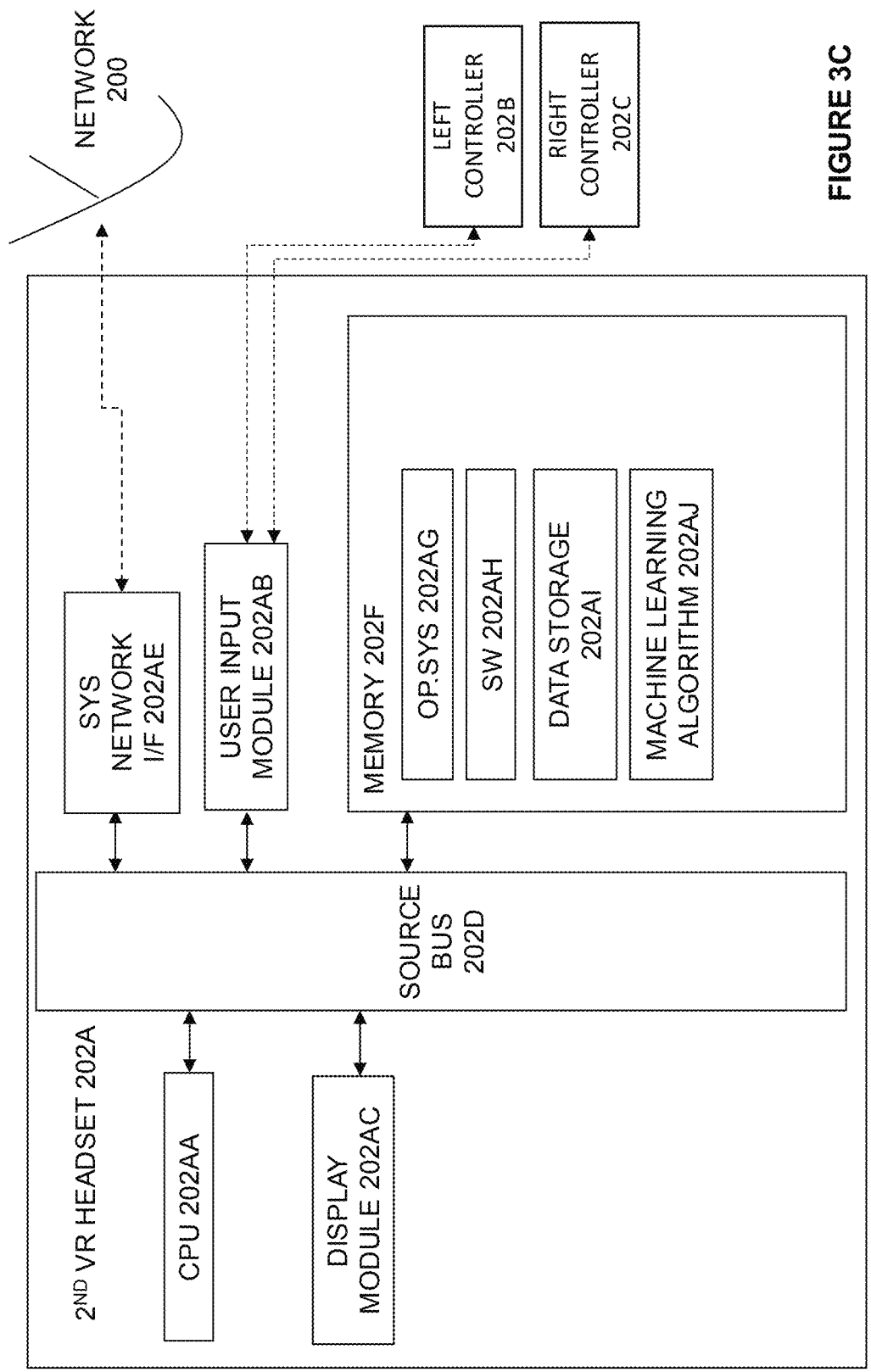
FIG. 3C is a hardware diagram presenting the second virtual reality device of FIG. 2.

Referring now generally to the Figures, and particularly to FIG. 2, FIG. 2 is a diagram presenting an electronic communications network 200 ("the network 200") connecting a plurality of devices in a second preferred embodiment of a system for practicing aspects of the invented method. It is noted that, while the system of FIG. 1 might be viewed as an environment for practicing the invented method which may not necessarily require much networking besides direct connections between devices, such as a station set up in a physiotherapist's office for a patient to use during an in-person appointment, the network 200 of FIG. 2 would be a preferred environment for practicing the invented method either in person or remotely. The devices connected to the network 200 of FIG. 2, which might be any kind of electronic communications network such as but not limited to the internet or a local area network (LAN), are broadly categorized into a 'patient side' which may include the VR headset 108A, the left VR controller 108B, the right VR controller 108C, the optional force plate 106 if included, and a 'therapist side' which may include the device 104 and also a second VR headset 202 further comprising a second VR headset 202A, a second left VR controller 202B, and a second right VR controller 202C (also, "the 2nd VR controllers 202B&C"), which may be worn and utilized by a therapist interacting with the patient 102. It is noted that, depending on particular device and network configurations, the VR controllers may connect directly to the VR headsets or have their own 'channel' for connecting with other elements of a same set of VR gear, or a set of VR gear may rely on a network connection such as WiFi or Bluetooth to make these connections; these Figures present each of these possibilities in the various included Figures to reflect this variable connectivity, with FIG. 2 presenting the controllers as connecting via the network 200, and the subsequent hardware diagrams of FIG. 3A through 3C presenting these as a user interface connection, analogous to a keyboard, mouse, or joystick. It is understood that as long as the relevant communicative couplings are present somehow, whether it's WiFi, Bluetooth, radio signals, infrared, actual cables, or something else, as long as the systems are connected in a manner sufficient to practice the invention as described herein, the exact configuration is a logistical concern that one skilled in the art of systems administration or other disciplines of device connectivity might recognize as relatively trivial. It is further noted that the network 200 is portrayed entirely from a hardware perspective, with software aspects of network administration such as IP addressing, networking protocols, firewalls, network security, and so forth assumed and anticipated as present in accordance with best practices as known by one skilled in the art for providing a secure and functional network environment.

Referring now generally to the Figures, and particularly to FIG. 3A, FIG. 3A is a block diagram of the device 104 of the system 100 of FIG. 1 and displaying together both hardware and software aspects thereof, wherein the device 104 comprises: a central processing unit or "CPU" 104A; a user input module 104B; a display module 104C; a software bus 104D bi-directionally communicatively coupled with the CPU 104A, the user input module 104B, the display module 104C; the software bus 104D is further bi-directionally coupled with a network interface 104E, enabling communication with alternate computing devices by means of the network 100; and a memory 104F. The user input module 104B facilitates communication to external human-operated data sources such as the VR gear 108 and the optional force plate 106 if included, in addition to the basic utility of connection to a control element for the device 104 itself, such as connection to a keyboard and/or mouse. The software bus 104D facilitates communications between the above-mentioned components of the device 104. The network interface 104E may provide connection to a network such as the internet; network connectivity is neither included nor excluded as an aspect of the invention and the device 104 may be internet-enabled but need not be, except where this may concern connection to another system 100 device, such as a WiFi, Bluetooth, or similar wireless connection to the VR gear 108 or the optional force plate 106 if included in lieu of a cable. It is noted that wireless connections, particularly to the VR gear 108, may be preferable at least to facilitate use of the VR gear 108 without tangling the patient 102 in cables, and it may also be preferred to conceal a force plate 106 cable or have a wireless force plate 106 connection also, to reduce potential trip hazards. It is further noted that a medical practitioner's office may have good reason to limit which in-office computers are internet-enabled at all, to make it easier to safeguard patients' medical data and reduce the possibility of introducing any computer viruses to sensitive devices on which patients' lives may sometimes depend. The memory 104F of the device 104 includes a software operating system OP.SYS 104G. The software operating system OP.SYS 104G of the device 104 may be selected from freely available, open source and/or commercially available operating system software, to include but not limited to a.) a Z8 G4 computer workstation marketed by Hewlett Packard Enterprise of San Jose, California and running a Red Hat Linux™ operating system marketed by Red Hat, Inc. of Raleigh, North Carolina; (b.) a Dell Precision™ computer workstation marketed by Dell Corporation of Round Rock, Texas, and running a Windows™ 10 operating system marketed by Microsoft Corporation of Redmond, Wash.; (d.) a Mac Pro workstation running MacOS X™ as marketed by Apple, Inc. of Cupertino, Calif.; or (e.) other suitable computational system or electronic communications device known in the art capable of providing networking and operating system services as known in the art. The exemplary software program SW 104H consisting of executable instructions and associated data structures is optionally adapted to enable the device 104 to perform, execute and instantiate all elements, aspects and steps as required of the device 104 to practice the invented method in its various preferred embodiments in interaction with other devices of the network 100. The memory 104F may further include storage for data gathered in accordance with the invented method, a data storage 104I. The memory 104F may further include a machine learning algorithm 104J or model, such as for modeling patient motion as indicated by the gathered data.

Referring now generally to the Figures, and particularly to FIG. 3B, FIG. 3B is a block diagram of the VR gear 108 of the system 100 of FIG. 1 and displaying together both hardware and software aspects thereof, wherein the computing environment of the VR gear 108 (generally located within the VR headset 108A) includes: a central processing unit or "CPU" 108AA; a user input module 108AB; a display module 108AC; a software bus 108AD bi-directionally communicatively coupled with the CPU 108AA, the user input module 108AB, the display module 108AC; the software bus 108AD is further bi-directionally coupled with a network interface 108AE, enabling communication with other computing devices such as the device 104 of the system 100; and a memory 108F. The user input module 108B facilitates communication to external human-operated data sources such as the left VR controller 108B and the right VR controller 108C, or other controller elements which may be used compatibly with the VR gear 108. The software bus 108D facilitates communications between the above-mentioned components of the VR gear 108. The network interface 108E may provide connection to a network such as the internet; network connectivity is neither included nor excluded as an aspect of the invention and the VR gear 108 may be internet-enabled but need not be, except where this may concern connection to another device, such as a WiFi, Bluetooth, or similar wireless connection to the device 104 or to the left VR controller 108B and/or the right VR controller 108C. It is noted that wireless connections, particularly to and from the VR gear 108, may be preferable at least to facilitate use of the VR gear 108 without tangling the patient 102 in cables. The memory 108F of the VR gear 108 may include a software operating system OP. SYS 108G suitable for operating a virtual reality device as generally known in the art. It is noted that some current examples of virtual reality equipment currently available which could be suitable for use as the VR gear 108 might include the Oculus Quest 2 as marketed by Meta of Menlo Park, CA, United States; the Sony PlayStation VR as marketed by Sony of Tokyo, Japan; the Valve Index VR Kit as marketed by Valve of Bellevue, WA, United States; or the HP Reverb G2 as marketed by Hewlett Packard of Palo Alto, CA, United States. It is further generally noted that, though essentially specialized wearable computing devices, any virtual reality device may further include components, features, or elements not represented in the diagram of FIG. 3B, including proprietary elements particular to that virtual reality console. It is further noted that the VR gear 108 need not be any of these commercially-available video-gaming consoles, and also that a similar device produced for a specific category of medical use instead of provided as a multifaceted consumer entertainment console could incorporate fewer frills and still retain the basic technological functionality necessary to practice of the invented method as described herein. The memory 102F of the VR gear 108 may include at least one software program SW 108H consisting of executable instructions and associated data structures optionally adapted to enable the VR gear 108 to perform, execute and instantiate all elements, aspects and steps as required of the VR gear 108 to practice the invented method in its various preferred embodiments in interaction with the rest of the system 100 as described. The memory 108F may further include storage for data gathered in accordance with the invented method, a data storage 108I. The memory 108F may further include a machine learning algorithm 108J or model, such as for modeling patient motion as indicated by the gathered data.

Referring now generally to the Figures, and particularly to FIG. 3C, FIG. 3C is a block diagram of the 2nd VR gear 202 of the network 200 of FIG. 2 and displaying together both hardware and software aspects thereof, wherein the computing environment of the 2nd VR gear 202 (generally located within a VR headset 202A) includes: a central processing unit or "CPU" 202AA; a user input module 202AB; a display module 202AC; a software bus 202AD bi-directionally communicatively coupled with the CPU 202AA, the user input module 202AB, the display module 202AC; the software bus 202AD is further bi-directionally coupled with a network interface 202AE, enabling communication with the network 200 or other devices; and a memory 202F. The user input module 202B facilitates communication to external human-operated data sources such as the left VR controller 202B and the right VR controller 202C, or other controller elements which may be used compatibly with the 2nd VR gear 202. The software bus 202D facilitates communications between the above-mentioned components of the 2nd VR gear 202. The network interface 202E may provide connection to a network such as the internet; network connectivity is neither included nor excluded as an aspect of the invention and the 2nd VR gear 202 may be internet-enabled but need not be, except where this may concern connection to another device, such as a WiFi, Bluetooth, or similar wireless connection to the network 200 or to the left VR controller 202B and/or the right VR controller 202C. It is noted that wireless connections, particularly to and from the 2nd VR gear 202, may be preferable at least to facilitate use of the 2nd VR gear 202 without tangling a user in cables. The memory 202F of the 2nd VR gear 202 may include a software operating system OP. SYS 202G suitable for operating a virtual reality device as generally known in the art. It is noted that some current examples of virtual reality equipment currently available which could be suitable for use as the 2nd VR gear 202 might include the Oculus Quest 2 as marketed by Meta of Menlo Park, CA, United States; the Sony PlayStation VR as marketed by Sony of Tokyo, Japan; the Valve Index VR Kit as marketed by Valve of Bellevue, WA, United States; or the HP Reverb G2 as marketed by Hewlett Packard of Palo Alto, CA, United States. It is further generally noted that, though essentially specialized wearable computing devices, any virtual reality device may further include components, features, or elements not represented in the diagram of FIG. 3C, including proprietary elements particular to that virtual reality console. It is further noted that the 2nd VR gear 202 need not be any of these commercially-available video-gaming consoles, and also that a similar device produced for a specific category of medical use instead of provided as a multifaceted consumer entertainment console could incorporate fewer frills and still retain the basic technological functionality necessary to practice of the invented method as described herein. The memory 102F of the 2nd VR gear 202 may include at least one software program SW 202H consisting of executable instructions and associated data structures optionally adapted to enable the 2nd VR gear 202 to perform, execute and instantiate all elements, aspects and steps as required of the 2nd VR gear 202 to practice the invented method in its various preferred embodiments in interaction with the rest of the network 200 as described. The memory 202F may further include storage for data gathered in accordance with the invented method, a data storage 202I. The memory 202F may further include a machine learning algorithm 202J or model, such as for modeling patient motion as indicated by the gathered data.

Figure 4:
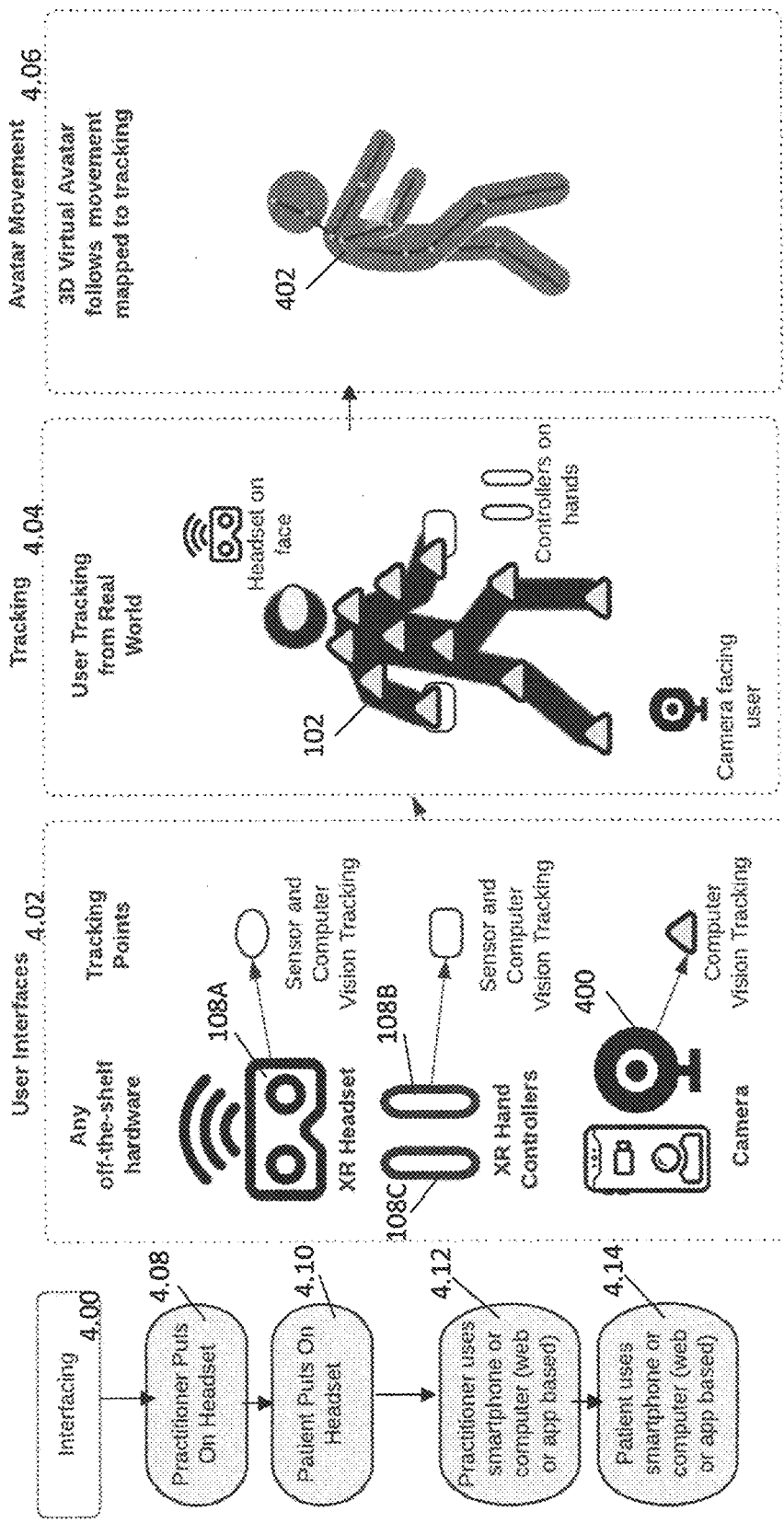
FIG. 4 is a first chart presenting various aspects of the invented method as practiced within the invented system of FIG. 1, particularly pertaining to forming connections between user actions and digital modeling of the virtual reality gear.

Referring now generally to the Figures, and particularly to FIG. 4, FIG. 4 is a first chart presenting various aspects of the invented method as practiced within the invented system of FIG. 1, particularly pertaining to forming connections between user actions and digital modeling of the virtual reality gear. This chart can be organized into an Interfacing column 4.00 at the leftmost side of the chart, a User Interfaces column 4.02 second-to-left, a Tracking column 4.04 at the second-to-right, and an Avatar Movement column 4.06 at the rightmost side of the chart. Included under the Interfacing column 4.00: in sub-element 4.08, the practitioner (therapist) puts on a VR headset such as the 2nd VR headset 202A; in sub-element 4.10, the patient 102 puts on a VR headset such as the VR headset 108A. Alternatively, some aspects of the invented method might be performable without full sets of VR equipment, and might use alternative equipment such as a computer, phone, or tablet. A smartphone in particular includes features for enabling augmented reality functions, such as gyroscopes and GPS. Therefore, also included under the Interfacing column 4.00: in sub-element 4.12, the practitioner (therapist) uses a smartphone or computer to implement a web or app based implementation, and in sub-element 4.14, the patient 102 uses a smartphone or computer to implement a web or app based implementation. It is noted that depending upon the technological environment, these sub-elements might also be mix-and-matched, for instance if one party has VR gear but the other doesn't. In the User Interfaces column 4.02, a symbol key is provided for the visual presented in the Tracking column 4.04, specifically that a VR/AR/MR/XR headset, such as the VR headset 108A or the 2nd VR headset 202A, is represented as an oval; controllers such as the VR controllers 108B&C or the 2nd VR controllers 202B&C are represented as rounded rectangles; and body points detected by a camera 400 doing visual tracking are represented by triangles. It is noted that, while a camera was not presented in the hardware diagrams, a camera may be an additional input device utilized in the system 100 of FIG. 1, and may be accordingly communicatively coupled to an appropriate computing device as necessary for receiving and interpreting data generated by the camera 400 and utilizing the camera data in accordance with the method. In the Tracking column 4.04, an image of a user wearing a VR headset, holding controllers, and being tracked by a camera facing the user is presented, with the symbols as codified in the User Interfaces column 4.02 showing how the gear tracks the position of the user's body parts. In the Avatar Movement column 4.06, the body parts tracked in the Tracking column 4.04 are drawn in a virtual medium, such that the movement of the user's body as tracked is re-created in virtual rendering as a virtual avatar 402. It is noted that in this image the position of the virtual figure is not actually the same position as that of the user in the Tracking column 4.04, and the virtual avatar 402 is simply shown in some postural position; it is understood that the virtual avatar 402 may use the data as gathered according to this Figure to match the movement of a user as that user moves, or may alternatively be molded to present some other movement or position, such as to demonstrate to or guide the patient 102 in performing a particular exercise or stretch. It is noted that the camera 400 is another optional hardware component that might not be utilized in all embodiments of the invented system, but may provide further possibilities for functionality and data gathering.

Figure 5:
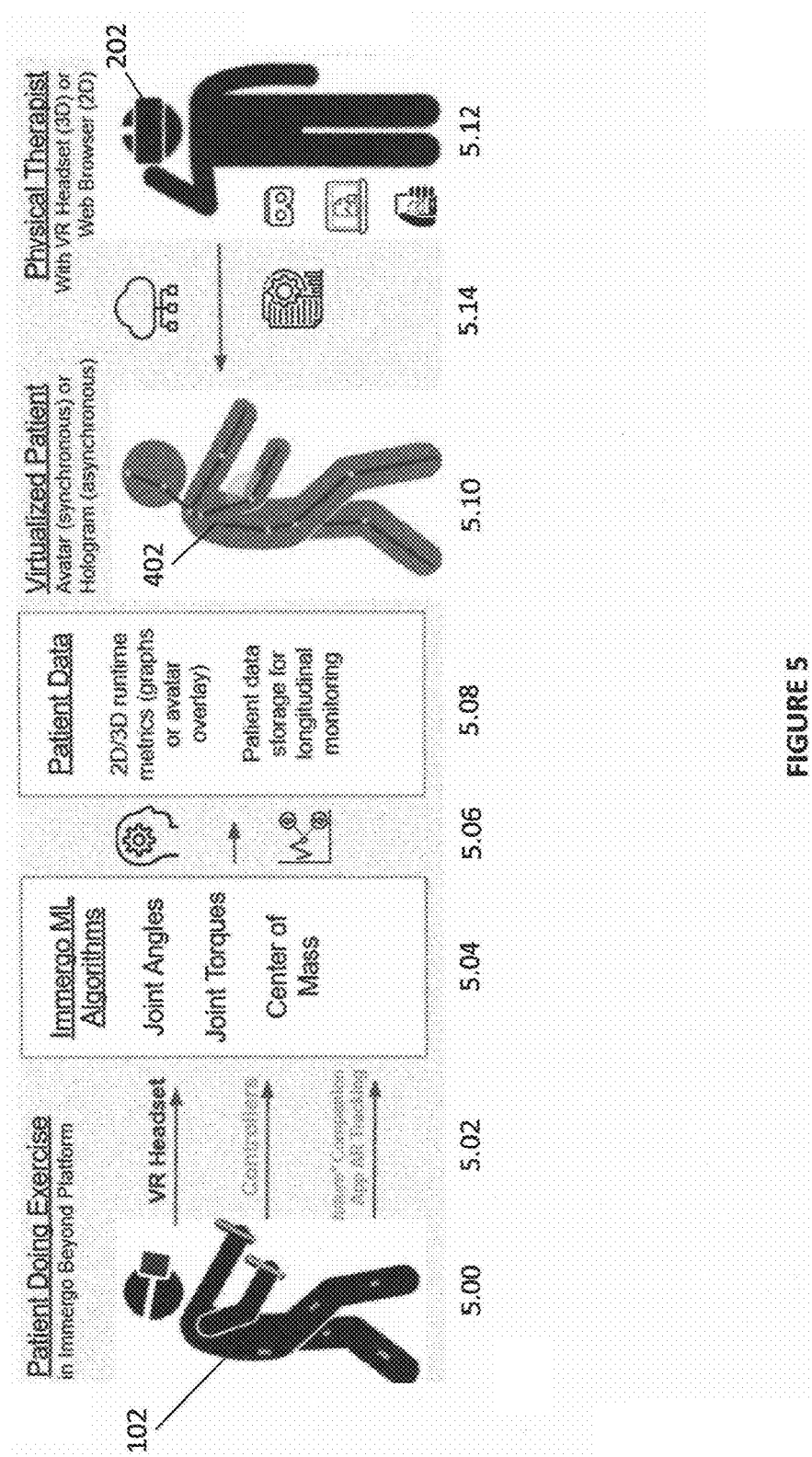
FIG. 5 is a second chart presenting various aspects of the invented method as practiced within the invented system of FIG. 2, particularly pertaining to patient and therapist interaction within a virtual 3D interface.

Referring now generally to the Figures, and particularly to FIG. 5, FIG. 5 is a second chart presenting various aspects of the invented method as practiced within the invented system of FIG. 2, particularly pertaining to patient and therapist interaction as processed through a virtual interface. In a first column 5.00 at the far left, the patient 102 is interacting with the VR gear 108 as shown. In a second column 5.02, arrows show data input from the VR gear 108 being gathered. In a third column 5.04, Machine Learning Algorithms are applied to this received data, such as to analyze joint angles, joint torques, and center of mass. In a fourth column 5.06, further algorithms may be applied. In a fifth column 5.10, the virtual avatar 402 is instantiated, utilizing the data and analysis generated in the previous columns proceeding from the left of the Figure. In a rightmost column 5.12, a therapist interacts with the 2nd VR gear 202 or another means of accessing the virtual avatar 402, allowing this therapist to utilize an interface represented in a second-to-right column 5.14 to observe the movements of the patient 102 as represented by the virtual avatar 402.

Figure 6:
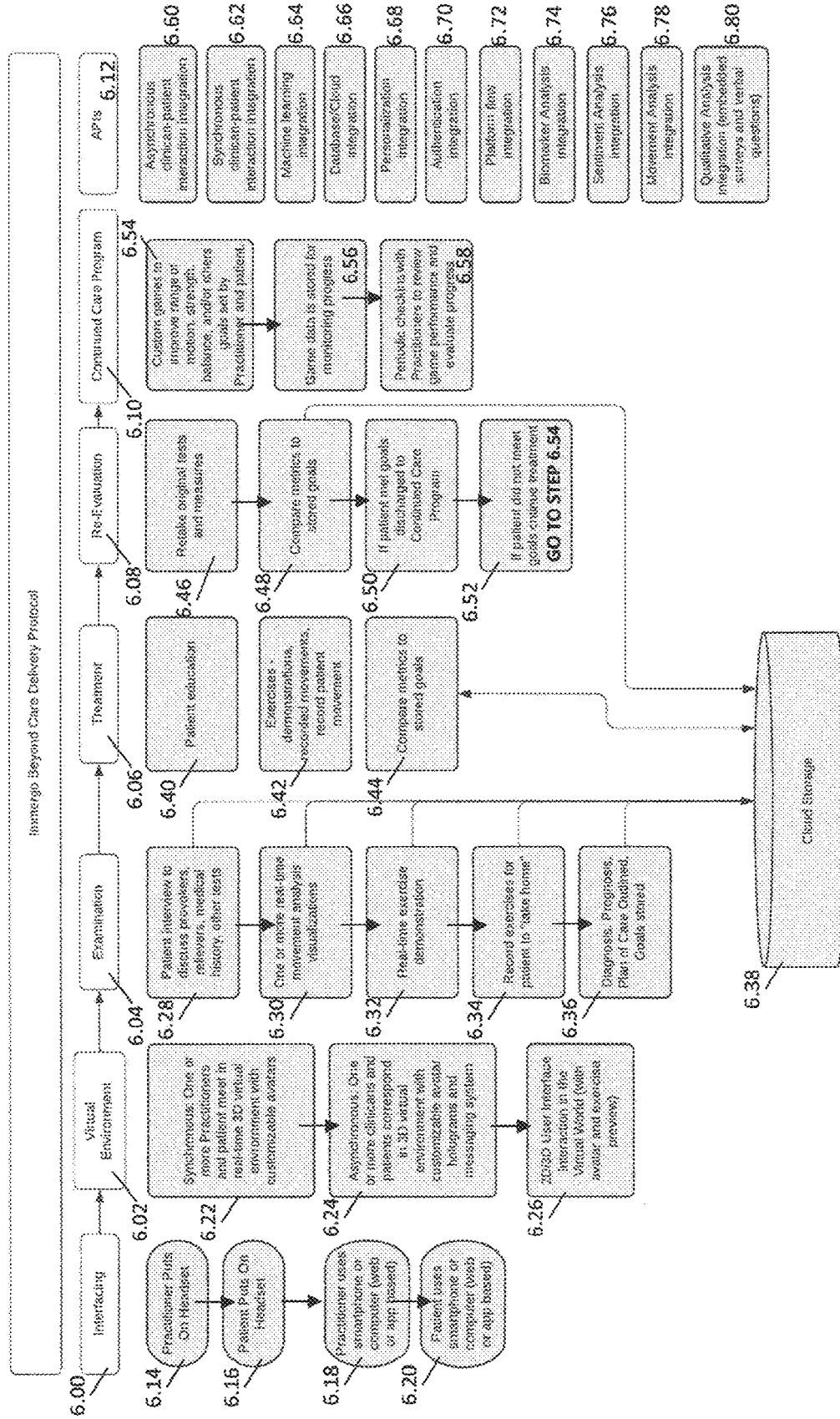
FIG. 6 is a third chart presenting various aspects of the invented method as practiced within the invented system of FIG. 1.

Referring now generally to the Figures, and particularly to FIG. 6, FIG. 6 is a third chart presenting various aspects of the invented method as practiced within the invented system of FIG. 1. This chart presents an overview of an examination and treatment protocol incorporating the invented method for utilizing VR technology in physical therapy. As presented across the top, the elements of this chart can broadly be read as sub-elements of the following series of categories or steps: an Interfacing 6.00 step, a Virtual Environment 6.02 step, an Examination 6.04 step, a Treatment 6.06 step, a Re-Evaluation 6.08 step, a Continued Care Program 6.10 step, and an Application Programming Interfaces 6.12 ("APIs 6.12") step. Included under Interfacing 6.00: in sub-element 6.14, the practitioner (therapist) puts on a VR headset such as the 2nd VR headset 202A; in sub-element 6.16, the patient 102 puts on a VR headset such as the VR headset 108A. Alternatively, some aspects of the invented method might be performable without full sets of VR equipment, and might use alternative equipment such as a computer, phone, or tablet. A smartphone in particular includes features for enabling augmented reality functions, such as gyroscopes and GPS. Therefore, also included under Interfacing 6.00: in sub-element 6.18, the practitioner (therapist) uses a smartphone or computer to implement a web or app based implementation, and in sub-element 6.20, the patient 102 uses a smartphone or computer to implement a web or app based implementation. It is noted that depending upon the technological environment, these sub-elements might also be mix-and-matched, for instance if one party has VR gear but the other doesn't. Under Virtual Environment 6.02, notable sub-elements include the following: in sub-element 6.22, a synchronous virtual meeting is conducted between one or more practitioners and the patient 102, within a real-time customizable digital environment, while in sub-element 6.24, the same parties might asynchronously correspond; in sub-element 6.26, a user (such as a therapist or the patient 102) interacts individually with a user interface alone. Under Examination 6.04, some key sub-elements include the following. In sub-element 6.28, there is a patient interview to discuss provokers, relievers, medical history, and other tests may be discussed or performed. In sub-element 6.30, one or more real-time movement analysis visualizations may be performed. In sub-element 6.32, one or more real-time exercise demonstrations may be performed. In sub-element 6.34, one or more exercises for a patient to 'take home' may be recorded. Sub-element 6.36 may include diagnosis, prognosis, plan of care outlining, and setting of goals. It is noted that any or all of these sub-elements of Examination 6.04 may be recorded in a cloud storage volume 6.38 for subsequent access, such as later reference. Under Treatment 6.06, some key sub-elements include the following. Sub-element 6.40 is patient education. Sub-element 6.42 is exercises, such as demonstrations, recorded movements, and recording of patient movement. Sub-element 6.44 includes comparing metrics to stored goals, such as in reference to the goals set at sub-element 6.36 and stored in the cloud storage 6.38. Under Re-Evaluation 6.08, some key sub-elements may include the following. At sub-element 6.46, the patient 102 may re-take the original tests and measures. At sub-element 6.48, the metrics from the re-taking of tests might be measured against previously set and stored goals. At sub-element 6.50, if the patient 102 has met the goals, the patient 102 may be discharged to the Continued Care Program 6.10. In sub-element 6.52, if the patient did not meet the goals, treatment may continue. Under Continued Care Program 6.10, some key sub-elements may include the following. At sub-element 6.54, there may be custom games to improve range of motion, strength, balance, and/or other goals set by the patient and practitioner. At sub-element 6.56, game data is stored for monitoring progress. At step 6.58, there are periodic check-ins to review game performance and evaluate progress. Under APIs 6.12, some key sub-elements may include the following. At sub-element 6.60, there is asynchronous clinician-patient interaction integration. At sub-element 6.62, there is synchronous clinician-patient interaction integration. At sub-element 6.64, there is machine learning integration. At sub-element 6.66, there is database/cloud integration. At sub-element 6.68, there is personalization integration. At sub-element 6.70, there is authentication integration. At sub-element 6.72, there is platform flow integration. At sub-element 6.74, there is Biomarker Analysis integration. At sub-element 6.76, there is Sentiment Analysis integration. At sub-element 6.78, there is Movement Analysis integration. At sub-element 6.80, there is Qualitative Analysis integration (embedded surveys and verbal questions).

Figure 7:
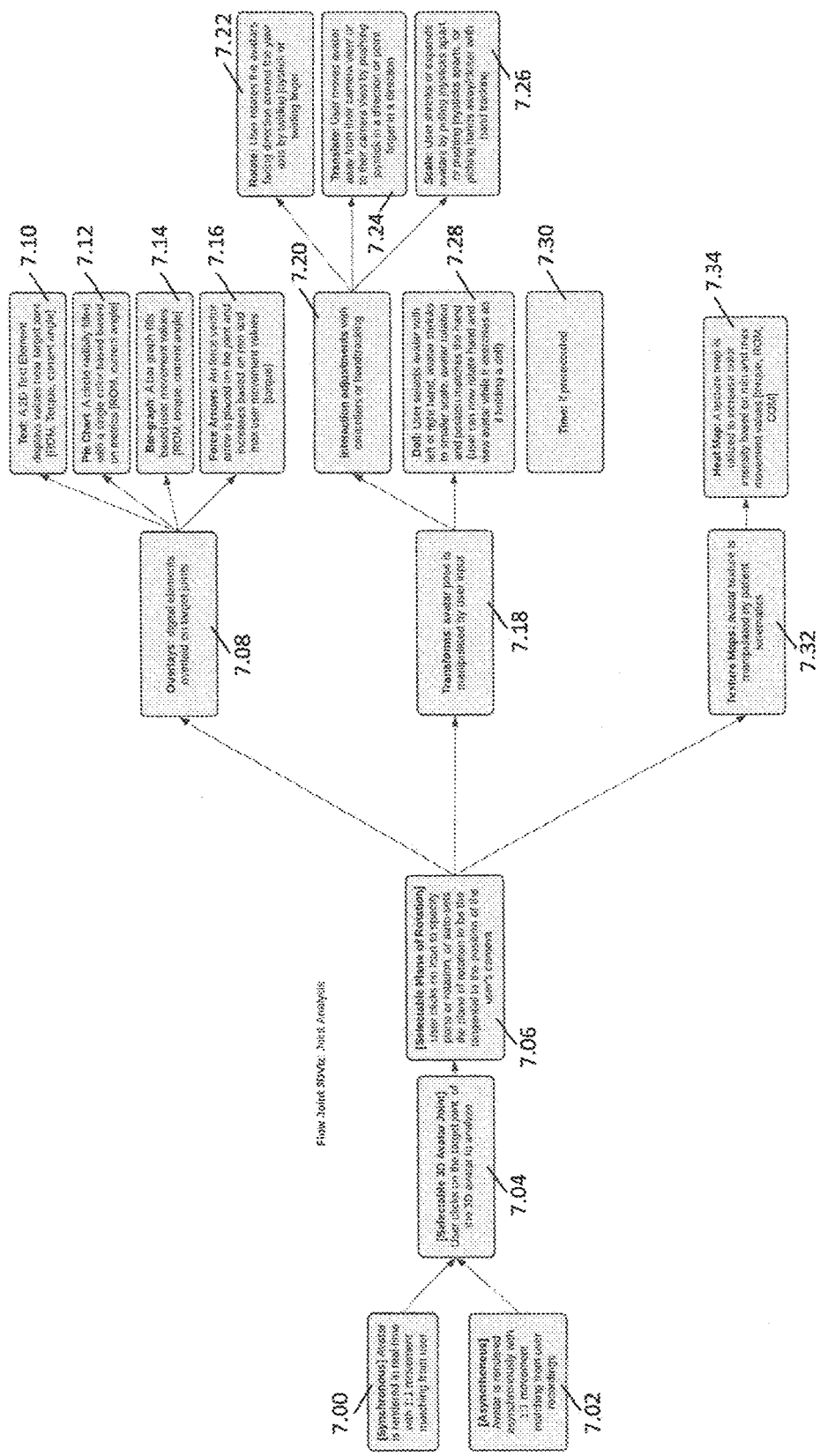
FIG. 7 is a fourth chart presenting various aspects of the invented method as practiced within the invented system of FIG. 1, pertaining particularly to analysis and assessment of a patient's joint health.

Referring now generally to the Figures, and particularly to FIG. 7, FIG. 7 is a fourth chart presenting various aspects of the invented method as practiced within the invented system of FIG. 1, pertaining particularly to analysis and assessment of a patient's joint health. Elements 7.00 and 7.02 present two alternative methods for the movement of the patient 102 to be observed utilizing the VR gear 108. In element 7.00, the movement of the patient 102 is rendered in real-time, as the patient 102 moves, and the virtual avatar 402 generated by the VR gear 108 imitates the detected motion of the patient 102 in a 1:1 correspondence, such that the virtual avatar 402 moves the same way the patient 102 moves, specifically enough for irregularities in the movement of the patient 102 to be observed by a physical therapist treating the patient 102. Alternatively, the movement of the patient 102 may be demonstrated asynchronously, such that the movement of the patient 102 is recorded by the VR gear 108 and can be played back later, as re-enacted by the virtual avatar 402, for observation. It is noted that the distinction between these two options is only whether the movement demonstration is being done 'live' or being recorded, and further that, while there are unique benefits to real-time interaction, a movement demonstration done 'live' could also be recorded for review later, such as for a therapist to study further offline, for the therapist and patient 102 to consider together from a third-person vantage-point (i.e. "see how your knee moved right there?"), or for a comparison later on to show improvement in the movement of a patient 102. In element 7.04, regardless of how the motion data was obtained, the virtual avatar 402 generated to imitate the motions of the patient 102 may be queryable, such that the patient 102 or their therapist can click or tap on parts of the virtual avatar 402 to view more information or analysis. For instance, if the knee of the virtual avatar 402 makes a certain motion of interest, a user could click on the virtual knee to learn more: view the raw data that led to the knee being rendered that way (very useful for debug), find out which device or combination of devices (such as the VR headset 108A, the left VR controller 108B, the right VR controller 108C, the force plate 106, etc.) detected the motion, or even view an analysis of why the computer 'thinks' this motion occurred and what it might mean about other structural elements' motion. For instance, most people might have experienced the common problem that if one has an injury (or even just muscle tension) in one leg, the other side may work harder to compensate; if one injures their left foot or leg, that affects their right leg also, not to mention their hips and back, which may do a lot of shifting of weight or posture to take stress off the unsteady left leg; all this can happen without the patient 102 even noticing, and soon the 'left-leg' injury has somehow expanded into full-body achy soreness as well. That dynamic of shifting posture to take work away from the injured left leg would show up in the movement of the patient 102, and in this example, the sore right hip (for instance) of the patient 102 might be queryable: 'Why is the right hip moving that way? Because the left hip is moving this way. Why is the left hip doing that? Because the left leg can't support the weight. Oh, well we know why that is, the left ankle got sprained.' Indeed, it can be very difficult, particularly with longstanding chronic pain, to figure out what is actually an injury (if it isn't obvious), and what other complaints (such as that sore right hip) might have arisen as an indirect result, caused by the body of the patient 102 compensating for, working around, or protecting the injured body part. In element 7.06, a user viewing the motion of the virtual avatar 402, such as a therapist or the patient 102, can control view perspective, such as presenting the motion from a specified rotational angle or zooming in or out. It is noted that providing flexibility of view perspective for observation and manipulation of a 3D virtual environment is well known at least in the art of computer graphics and video gaming, and one skilled in the art will appreciate both what view options may be appropriate or preferred, and the importance of providing these. At element 7.08, various overlays may be provided for further viewing options, such as digital elements overlaid on target joints. It is noted that digital environments such as video games also routinely include this feature, where an overlay view may be toggled to visualize a particular element more easily. It is noted that the overlay view may specifically provide information about a selected element, such as a data readout when a user clicks on and queries a virtual body part as described above, but that an overlay may also be a more generalized map for visualizing the whole system, such as relevant color-coding, a mapping of pictures of internal muscle structure or bone structure as understood by medicine onto a current postural position, or an ability for a therapist to 'mark up' the image. It is understood that those overlay features specifically mentioned here should not be construed as limiting, but rather as accessible examples. In element 7.10, some text is included as part of the overlay view, which may display values such as the ROM (range of motion), torque, or current angle. In element 7.12, a pie chart is included as an overlay element, namely a circle radially filled with a certain color based on a metric such as ROM or current angle. In element 7.14, a bar graph may be included as an overlay element for displaying values such as the ROM, torque, or current angle. In element 7.16, one or more force arrows may be overlaid on the virtual avatar 402 image to highlight aspects of the motion of the patient 102. It is further noted that these overlays might be applied in real-time, such that the patient 102 can even watch the overlays interpret or annotate their moves as they make them, or might be applied to recorded motion being played back asynchronously. Alternatively or additionally, element 7.18 includes transformations, namely the pose of the avatar being directly manipulated by user input other than the motion input generated by the patient 102, such as input by a therapist to show a movement to the patient 102. Element 7.20 is a further elaboration on the Transformations of element 7.18, specifically Interaction Adjustments utilizing controllers or handtracking, such as a therapist manipulating a pose of the virtual avatar 402 with their VR controller or with a similarly tracked motion of their hand. Further elaborating on that, element 7.22 indicates that a user such as the patient 102 or a therapist might rotate the avatar's facing direction around the yaw axis by twirling a joystick, a finger, or some other control. It is noted that the term 'yaw' is used here as a term of art regarding three-dimensional rotation, and this term is most commonly used in the context of aerospace; as an accessible example, a plane in flight might rotate itself in these three dimensions: rolling (i.e. a 'barrel roll'), pitching (i.e. pointing its nose upward or downward), or yawing (i.e. pointing its nose to one side or the other to change direction of travel). Element 7.24 indicates that the location of the virtual avatar 402 might also be adjusted, either by 'drag and dropping' the virtual avatar 402 elsewhere in the virtual setting, or by adjusting the camera, and suggests that a joystick or finger control might be used to implement this. It is noted that no limitation should be construed regarding which particular controls or keybindings may be assigned for performing which actions, except as stated in the claims. It is further noted that controls may vary depending on what interface is available to a user, just as someone playing a video game utilizing a joystick will utilize a different set of controls than one using a keyboard and mouse to play the same game might use. Element 7.26 represents a third option, namely scaling the size of the virtual avatar 402. Element 7.28 presents an additional or alternative option for transforming the virtual avatar 402, namely an option to turn the avatar into a 'doll' version that can be freely molded to show demonstrated motions, as though a user were holding a doll. Element 7.30 notes that time may also be a relevant dimension in this manipulation, particularly if the motion is prerecorded; for instance, the recording might be slowed down for a 'slow-motion replay'. It is noted that, since the discipline of physical therapy is concerned particularly with how the body of the patient 102 moves, and with adjusting that movement where necessary to improve the patient's health such as by building habits of moving differently, it may be a common tool in physical therapy practice for a therapist to demonstrate a posture or stretch for the patient 102 to imitate, or to observe the movement of the patient 102 and manually adjust how the patient 102 is positioned. This physical component can make telehealth physical therapy a particular challenge to therapist and patient, and giving these tools 'back' to physical therapy as practiced remotely, by providing a virtual equivalent as described above, might be considered a key benefit of the invention. Element 7.32 further mentions the feature of texture maps, i.e. mapping overlays onto the virtual avatar 402 which reflect aspects of a patient's movement. Element 7.34 further elaborates that this might be for instance a heat map, where color intensity or hue is mapped onto the virtual avatar 402 based on gathered movement data, such as based on minimum and maximum values of torque, ROM, or COM. This visualization might make it easier for the patient 102 and/or a therapist to see patterns and points of interest regarding the movement of the patient 102.

Figure 8:
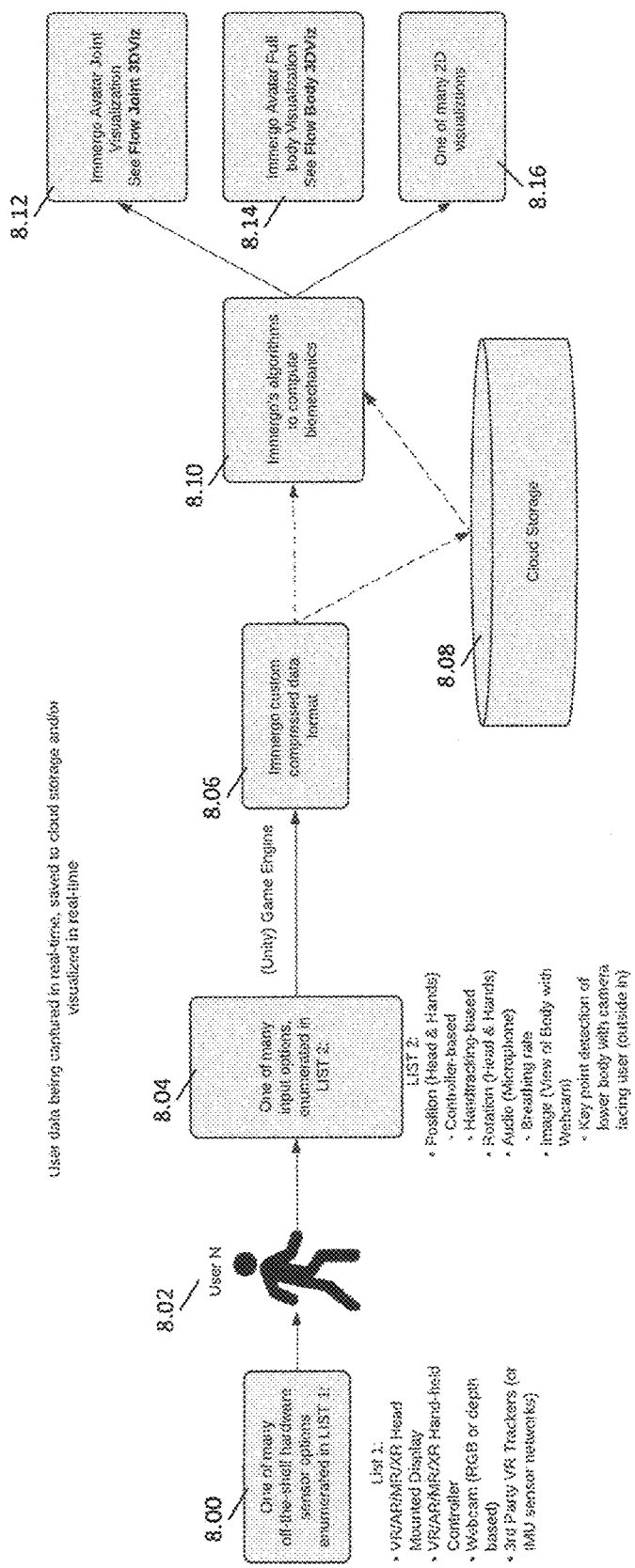
FIG. 8 is a fifth chart presenting various aspects of the invented method as practiced within the invented system of FIG. 1, pertaining particularly to capturing user data over time.

Referring now generally to the Figures, and particularly to FIG. 8, FIG. 8 is a fifth chart presenting various aspects of the invented method as practiced within the invented system of FIG. 1, pertaining particularly to capturing user data over time. In element 8.00, a suitable hardware environment is established, such as by utilizing items from the following list: VR/AR/MR/XR Head Mounted Display, VR/AR/MR/XR Hand-held Controller, Webcam (RGB or depth based), 3rd Party VR Trackers (IMU sensor networks). It is noted that this aspect is represented in the earlier hardware diagrams as the VR gear 108, and that the VR headset 108A and VR controllers 108B&C, and that any sort of device considered suitable as known in the art might be utilized, of which all these are just examples. In element 8.02, a user N, such as the patient 102 or a therapist, puts on, starts up, or otherwise interfaces with the equipment of element 8.00. In element 8.04, the user N provides input to the equipment of element 8.00, such as by moving parts of their body that the equipment is coupled to or held by, moving parts of their body otherwise visible to the equipment (such as moving one's hand within view of a motion-tracking camera interface), speaking or breathing within range of audio equipment such as a microphone, and so on as presented in LIST 2 adjacent to element 8.04. The input generated by the user N in element 8.04 may be introduced within the software structure of a game engine (such as a game engine constructed in Unity). At element 8.06, the received input is encoded in a proprietary data compression format. At element 8.08, the received and encoded input might be stored in Cloud Storage. At element 8.10, regardless of whether the data was also stored in Cloud Storage, algorithms are applied to compute biomechanics. At element 8.12, a visualization of a detected joint such as an elbow or knee may be generated based on the previously processed input data. At element 8.14, a full body visualization may be generated. At element 8.16, one of many 2D visualizations might be generated.

Figure 9:
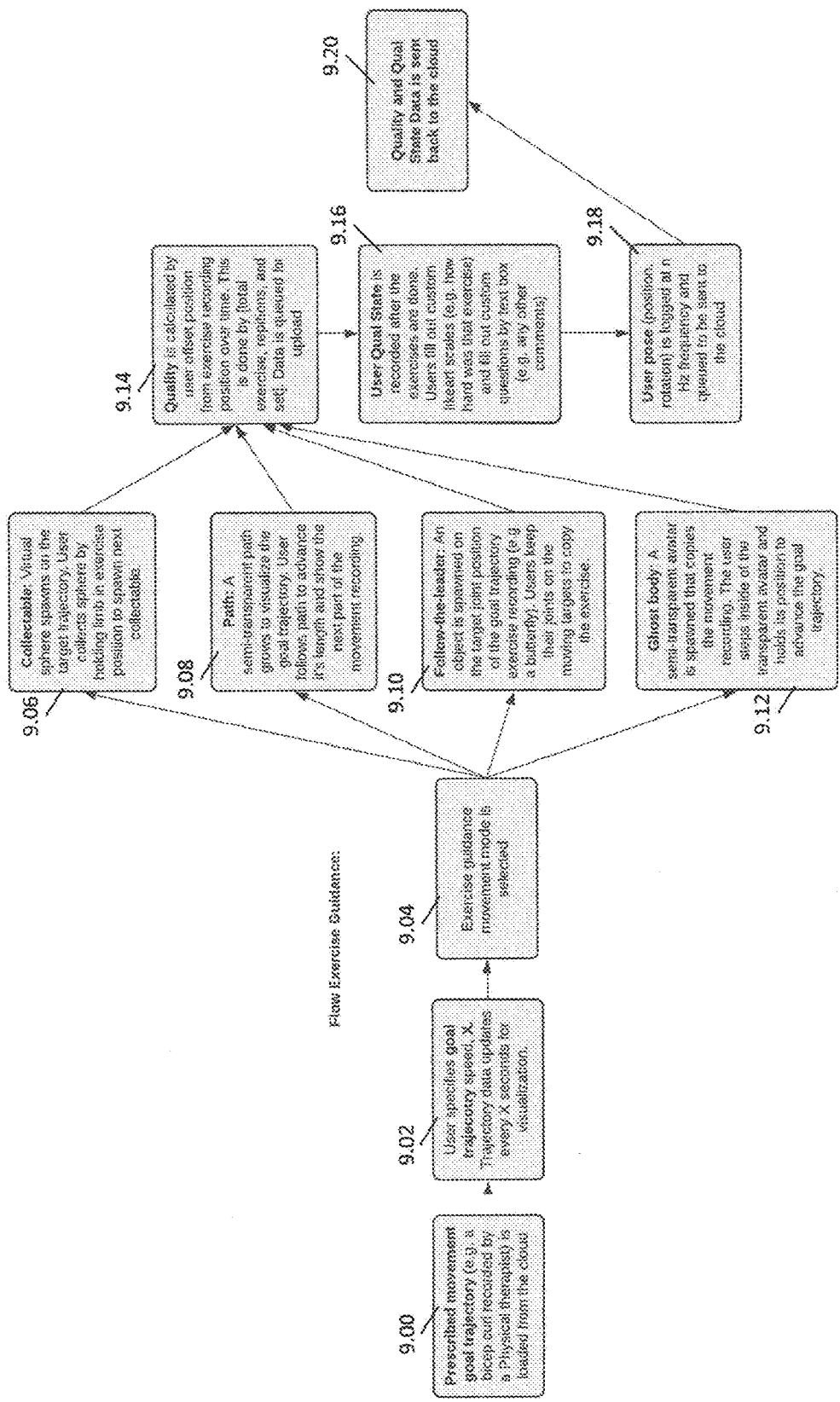
FIG. 9 is a sixth chart presenting various aspects of the invented method as practiced within the invented system of FIG. 1, particularly pertaining to flow exercise guidance.

Referring now generally to the Figures, and particularly to FIG. 9, FIG. 9 is a sixth chart presenting various aspects of the invented method as practiced within the invented system of FIG. 1, particularly pertaining to flow exercise guidance. At element 9.00, a prescribed movement goal trajectory is loaded, such as from cloud storage; this may be an item of recorded movement data, such as a bicep curl demonstration recorded by a physical therapist. At element 9.02, a goal trajectory speed X is specified by a user, which sets updating of the visualization with current trajectory data every X seconds. At element 9.04, an exercise guidance movement mode is selected. At element 9.06, a 'collectable' exercise format may be instantiated, such that a user such as the patient 102 is tasked to retrieve a virtual object such as a generated virtual sphere; for instance, if the patient 102 needs practice in bending down, the sphere may appear near the floor, requiring the patient 102 to practice their bending down to retrieve the sphere. At element 9.08, a 'path' exercise format may be instantiated, such that a user such as the patient 102 is presented with a semi-transparent path visualization, and tasked to trace the presented path with their input motion. The path may be shown only partially at a time, and extended as the exercise progresses. At element 9.10, a 'follow-the-leader' exercise format may be instantiated, such that an object appears in the virtual environment that a user such as the patient 102 is tasked to follow the movements of. At element 9.12, a 'ghost-body' exercise may be instantiated, wherein a semi-transparent avatar appears in the virtual environment that copies the movement recording, such as a demonstrated movement provided by a therapist, and a user such as the patient 102 is tasked to step inside the semi-transparent avatar and move such that their detected body remains inside the semi-transparent avatar body. At element 9.14, following an exercise, the quality of the exercise performance by the patient 102 is assessed. At element 9.16, the quality assessment is recorded, and the patient 102 may be queried about how hard they found the exercise to complete, or asked to provide other comments. At element 9.18, the current pose or position of the user is logged at n Hz frequency, and logged to be sent to the cloud or other data storage. At element 9.20, the recorded data is sent to the cloud or other data storage.

Figure 10:
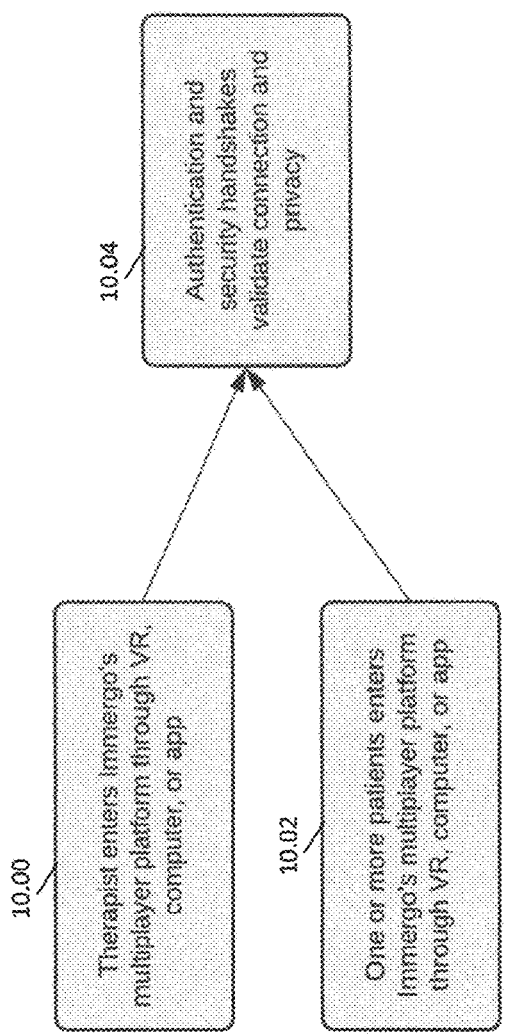
FIG. 10 is a seventh chart presenting various aspects of the invented method as practiced within the invented system of FIG. 1, particularly pertaining to a therapist and patient session.

Referring now generally to the Figures, and particularly to FIG. 10, FIG. 10 is a seventh chart presenting various aspects of the invented method as practiced within the invented system of FIG. 1, particularly pertaining to a therapist and patient session. In element 10.00, a therapist enters a virtual multiplayer platform through virtual reality, augmented reality, a computer, an application, or other suitable means known in the art. In element 10.02, the patient 102, or even multiple patients, enter a virtual multiplayer platform through virtual reality, augmented reality, a computer, an application, or other suitable means known in the art. In element 10.04, authentication and security handshakes validate connection and privacy for all of these connections.

Figure 11:
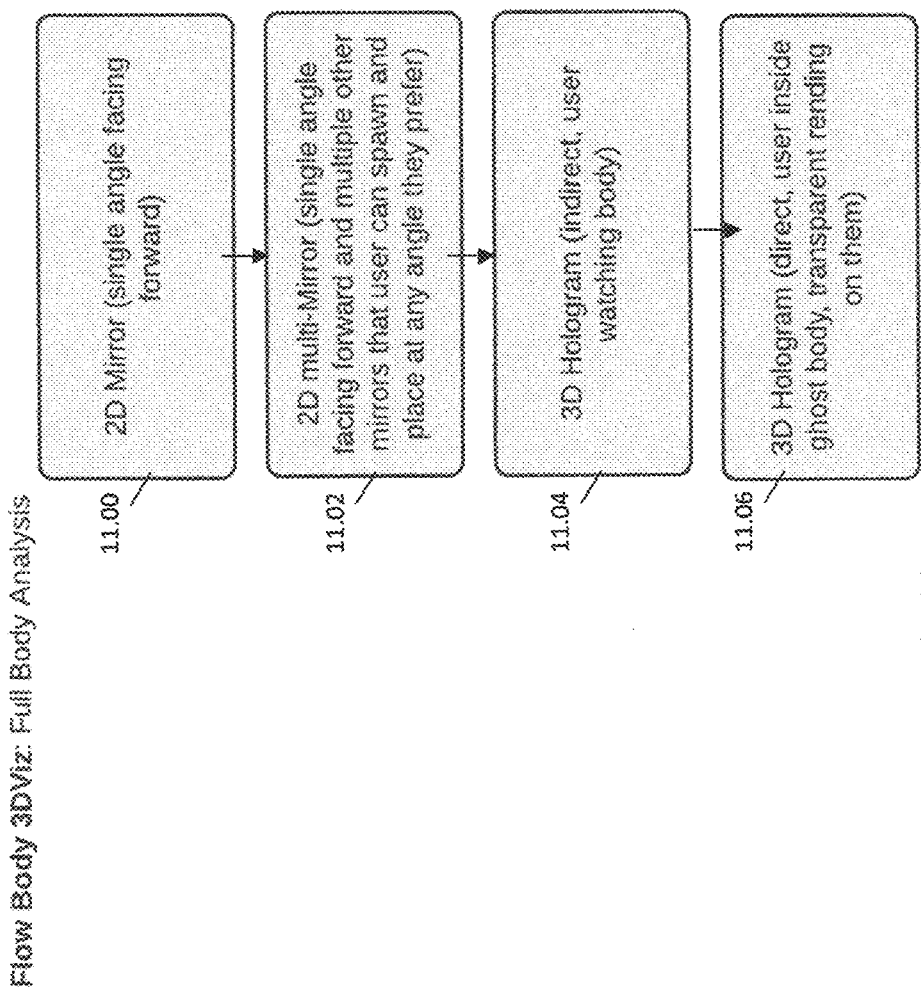
FIG. 11 is an eighth chart presenting various aspects of the invented method as practiced within the invented system of FIG. 1, particularly pertaining to full body analysis.

Referring now generally to the Figures, and particularly to FIG. 11, FIG. 11 is an eighth chart presenting various aspects of the invented method as practiced within the invented system of FIG. 1, particularly pertaining to full body analysis. Each element represents an alternative possible view option for presentation of the virtual avatar 402. In element 11.00, a two-dimensional mirror view is presented, which shows the subject from one angle facing forward, as though the subject were looking into a full-length wall mirror. In element 11.02, a two-dimensional multi-mirror option is presented, which may include or consist of a single angle facing forward view and multiple other 'mirrors' that can be generated and placed at other angles to show other views, like the multiple mirrors one might see and utilize in a fitting room for instance. In element 11.04, the option is presented of a three-dimensional hologram view, which may comprise or include a reflection of the subject's whole body from a third-person perspective, as though the subject were watching someone else. In element 11.06, a 'ghost body' option is presented, wherein a three-dimensional avatar body is projected around the viewpoint of the user, as though the user were wearing a virtual suit of armor. It is noted that these are just some non-limiting examples of interest, and that other view options and useful ways to render the virtual avatar 402 are possible as well.

Figure 12:
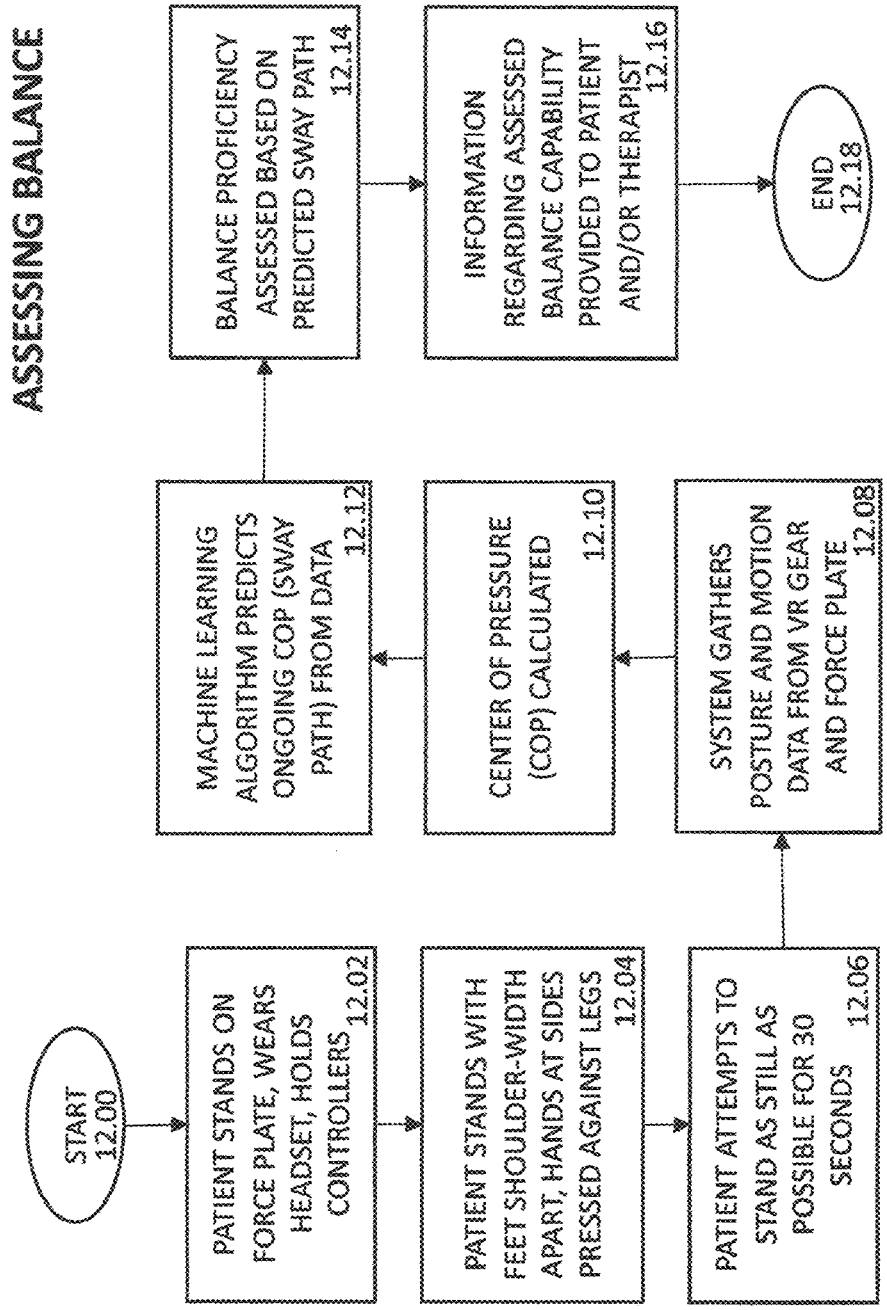
FIG. 12 is a process chart presenting one preferred procedure for assessing a user's balance capability utilizing the system of FIG. 1.

Referring now generally to the Figures, and particularly to FIG. 12, FIG. 12 is a process chart presenting one preferred procedure for assessing a user's balance capability utilizing the system of FIG. 1. At step 12.00, the process starts. At step 12.02, the patient 102 stands on optional the force plate 106 (if included), wears the VR headset 108A, holds the left VR controller 108B with their left hand, and holds the right VR controller 108C with their right hand. At step 12.04, the patient 102 stands with their feet shoulder-width apart and their hands at their sides pressed against the sides of their legs. At step 12.06, the patient 102 attempts to stand as still as they are able to. At step 12.08, while the patient 102 stands still, the system 100 measures any motion of the body of the patient 102, such as shifting off balance, swaying, and so on; even if the posture of the patient 102 may appear solid to a human observer, the optional force plate 106 (if included) and VR gear 108 may pick up minute weight shifts or patterns or compensations in balance that could indicate information about the posture and balance of the patient 102, and even indicate how likely the patient 102 may be to lose their balance in less ideal circumstances. It may even be possible to determine patterns from this gathered data, such as whether the patient 102 might favor one side or another, which structural elements of the body of the patient 102 may be receiving too much stress (such as a weaker muscle on one side than the other, which could result in a certain pattern of faltering or compensation), or similar, when interpreted by one skilled in the art of physical therapy who knows what to look for. At step 12.10, the center of pressure (COP) is calculated. At step 12.12, the machine learning algorithm predicts the ongoing center of pressure based on the gathered data. At step 12.14, the patient's balance proficiency is assessed based on the gathered data, particularly how much the patient 102 might be expected to sway and how, as predicted by the machine learning algorithm from how much and how the patient 102 sways in the gathered data. In step 12.16, this information is provided to the patient 102 and therapist, to be acted upon. At step 12.18, the process ends.

While selected embodiments have been chosen to illustrate the invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment, it is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

We claim:

1. A client device comprising:
    an augmented reality user set ("the user set"), the user set comprising a headset and an additional positional feedback device, the positional feedback device comprising a plurality of body element positional sensors ("the plurality of sensors") communicatively coupled with the headset, wherein the user set is configured to be worn by a human user and to generate and transmit relative body part dynamic positional information describing a dynamic kinesiologic action of the user's body;
    one or more processors bi-directionally communicatively coupled by a communications module with the user set; and
    a memory bi-directionally communicatively coupled by the communications module with the one or more processors and the user set, the memory storing software executable instructions executing on the client device, the software executable instructions when executed by the one or more processors cause the client device to:
        access a video segment directing the client system to dynamically visually render a user avatar derived from and dynamically responsive to kinesiologic relative body element positional information generated by and received from the plurality of sensors;
        transmit to the headset a sequence of data frames from a data stream program, the data stream program generated under the direction of a coaching practitioner ("the coach"), the data stream program presenting at least one personalized body parts movement pathway ("the pathway") indicating at least one recommended kinesiologic path of at least two internal anatomical elements of the user, wherein the sequence of data frames provides kinesiologic and positioning information of a modeling avatar for rendering by the headset, the modeling avatar adapted to dynamically present to the user via the headset aspects of the at least one personalized movement pathway; and
        display an interactive dynamic overlay of the modeling avatar over the user avatar by the headset, the interactive overlay displayed in association with a plurality of dynamically updated kinesiologic body part positional information received by the headset from the plurality of sensors, wherein the dynamically updated kinesiologic body part positional information generated by the user set is derived from the plurality of dynamically kinesiologic body part positional information generated by the plurality of sensors of the positional feedback device and received and integrated into the user avatar by the one or more processors.

2. The client device of claim 1, wherein the data stream program contains information derived from an earlier dynamically updated kinesiologic body element positional information received previous to a coaching session during which the user avatar is displayed.

3. The client device of claim 2, wherein the user set dynamically generated at least a portion of the updated kinesiologic body element positional information received previous to the coaching session.

4. The client device of claim 1, wherein the data stream program contains information that modifies a rendering of the modeling avatar on the basis of at least a portion of the dynamically updated kinesiologic body element positional information received from the user set during a same coaching session during which the user avatar is displayed.

5. The client device of claim 1, wherein the data stream program contains information that modifies a rendering of the modeling avatar on the basis of at least a portion of the dynamically updated kinesiologic body part positional information received from the user set during an earlier observed therapeutic session.

6. The client device of claim 1, wherein the data stream program contains information describing a full range of preferred motion personalized for an identified user.

7. The client device of claim 1, wherein the data stream program contains information describing a modified range of a preferred limited range of motion personalized for the user.

8. The client device of claim 1, wherein the data stream program contains information enabling the client device to dynamically vary a rendered range of motion on the bases of updated kinesiologic body element positional information generated by the plurality of sensors within a same therapeutic session.

9. The client device of claim 1, further comprising the one or more processors receiving an informational update to the data stream program, wherein the informational update provides information to the client device that enables a revision of the rendering of at least one recommended kinesiologic path of the positioning information of the modeling avatar adapted for rendering by the headset.

10. The client device of claim 9, wherein the informational update information is received and applied by the client device during a same coaching session.

11. The client device of claim 1, further comprising the memory containing additional software executable instructions that when executed by the one or more processors enable the client device to provide alternate avatar positioning information of two or more modeling avatars for rendering by the headset, wherein each modeling avatar is adapted to dynamically present to the user via the headset aspects of an alternate personalized movement pathway.

12. The device of claim 1, further comprising:
the user set further comprising an audio data rendering module ("audio module") coupled with the one or more processors; and
additional instructions of the software executable instructions that when executed by the one or more processors cause the client device to transmit audio data to the audio module.

13. The client device of claim 12, wherein the audio data is generated from the data stream program.

14. The client device of claim 12, wherein the audio data is sourced externally from the client device.

15. The client device of claim 14, wherein each data stream program includes a respective video sequence information and a respective audio sequence information, and the audio sequence information is adapted for rendering by the audio module.

16. A method of rendering interactive overlays within a movement coaching session, the method comprising:
accessing by one or more processors that direct a client system to dynamically visually render a user avatar at a headset from information partially derived from and dynamically responsive to a plurality of dynamically updated body parts positional information generated by a plurality of position sensors of the client system;
transmitting to the headset a sequence of data frames from a data stream program, wherein a plurality of the data frames include positioning information of a modeling avatar for rendering by the headset, the modeling avatar generated under the direction of a movement coach, the modeling avatar presenting at least one personalized pathway indicating recommended kinesiologic paths of at least two internal anatomical elements of an intended human user, the modeling avatar adapted to dynamically present to the human user via the headset aspects of the at least one personalized movement pathway; and
displaying an interactive dynamic overlay of the modeling avatar over the user avatar by the headset, the interactive dynamic overlay of the modeling avatar displayed in association with the dynamically updated body parts positional information positional information generated by the plurality of sensors of the positional feedback device.

17. The method of claim 16, further comprising establishing, by the one or more processors, a communication channel with a session management system, and wherein at least a portion of the sequence of data frames rendered by the headset are received by the client device over the established communication channel.

18. The method of claim 16, wherein the one or more processors are adapted to at least partially render a virtual reality environment by means of the headset.

19. The method of claim 16, wherein the modeling avatar is at least partly generated under the direction of a wellness practitioner while the user and the wellness practitioner are in a movement coaching session in real time.

20. The method of claim 19, wherein the modeling avatar is at least partly generated under the direction of a wellness practitioner while the user and the wellness practitioner is co-located during the movement coaching.

21. The method of claim 16, wherein at least a portion of the sequence of data frames of the modeling avatar are recorded prior to the initiating of the display of the interactive dynamic overlay of the modeling avatar over the user avatar.

22. The method of claim 16, wherein the modeling avatar is at least partly generated under the direction of the user while the user reviews movements in real time, wherein relative body element dynamic positional information is integrated into the sequence of data frames of the data stream program.

23. The method of claim 16, further comprising:
the modeling avatar is at least partly generated under the direction of the user by integration of at least a portion of the dynamic positional information into the sequence of data frames of the data stream program; and;
the user records in the client system a selection of the positional information generated by the plurality of body element position sensors of the client system in real time.

24. A non-transitory computer-readable medium comprising computer code instructions stored thereon, the computer code instructions, when executed by one or more processors, cause the one or more processors to:
access a video segment directing a client system to dynamically visually render a user avatar at a headset information partially derived from and dynamically responsive to positional information generated by a plurality of body element position sensors of the client system;
transmit to the headset a sequence of data frames from a data stream program, wherein a plurality of the data frames include positioning information of a modeling avatar for rendering by the headset, the modeling avatar generated under the direction of a wellness practitioner, the modeling avatar presenting at least one personalized movement pathway indicating recommended kinesiologic paths of at least two internal anatomical elements of an intended human user, the modeling avatar adapted to dynamically present to the user via the
headset aspects of a personalized movement path; and
display an interactive dynamic overlay of the modeling
avatar over the user avatar by the headset, the interactive overlay displayed in association with dynamically
updated positional information.

\* \* \* \* \*